(12) United States Patent
Sawyer et al.

(10) Patent No.: US 12,742,141 B2
(45) Date of Patent: Sep. 22, 2026

(54) DEVICES, SYSTEMS, AND METHODS RELATING TO PRESSURIZED PERFUSION-ENABLED BIO-REACTORS

(71) Applicant: University of Florida Research Foundation, Inc., Gainesville, FL (US)

(72) Inventors: Wallace Gregory Sawyer, Gainesville, FL (US); Jack E. Famiglietti, Gainesville, FL (US); Duy T Nguyen, Gainesville, FL (US); Diego Ivan Pedro, Gainesville, FL (US); Ryan A. Smolchek, Gainesville, FL (US); Juan Manuel Urueña Vargas, Gainesville, FL (US)

(73) Assignee: University of Florida Research Foundation, INC., Gainesville, FL (US)

( * ) Notice: Subject to any disclaimer, the term of this patent is extended or adjusted under 35 U.S.C. 154(b) by 522 days.

(21) Appl. No.: 18/285,779

(22) PCT Filed: May 18, 2022

(86) PCT No.: PCT/US2022/072390
§ 371 (c)(1),
(2) Date: Oct. 5, 2023

(87) PCT Pub. No.: WO2022/256768
PCT Pub. Date: Dec. 8, 2022

(65) Prior Publication Data

US 2024/0368518 A1 Nov. 7, 2024

Related U.S. Application Data

(60) Provisional application No. 63/195,042, filed on May 30, 2021.

(51) Int. Cl.
*C12M 1/00* (2006.01)
*C12M 1/12* (2006.01)

(52) U.S. Cl.
CPC ............ *C12M 29/10* (2013.01); *C12M 23/06* (2013.01); *C12M 23/38* (2013.01); *C12M 25/14* (2013.01); *C12M 37/04* (2013.01)

(58) Field of Classification Search
CPC ...... C12M 29/10; C12M 29/14; C12M 23/06; C12M 23/38; C12M 25/14; C12M 37/04
See application file for complete search history.

(56) References Cited

U.S. PATENT DOCUMENTS

2017/0009207 A1 1/2017 Shamir et al.
2019/0211294 A1 7/2019 Karnieli
(Continued)

FOREIGN PATENT DOCUMENTS

WO WO 2017/123788 A2 7/2017
WO WO 2019/157356 A1 8/2019

OTHER PUBLICATIONS

International Search Report and Written Opinion Received in PCT/US2022/072390, Mailed on Jul. 22, 2022.

*Primary Examiner* — Michael L Hobbs
(74) *Attorney, Agent, or Firm* — Thomas Horstemeyer LLP.

(57) ABSTRACT

The present disclosure provides for devices, systems, and methods relating to positive pressure perfusion-enabled bioreactors. Devices, systems, and methods as described here provide for improved culture of biological samples, thereby improving their viability for diagnostic, clinical, and research purposes. In certain aspects, devices, systems, and methods as described here provide for improved transport (such a shipping) of biological samples, thereby improving
(Continued)

their viability for diagnostic, clinical, and research purposes once arrived at their destination.

18 Claims, 16 Drawing Sheets

(56) References Cited

U.S. PATENT DOCUMENTS

| | | | | |
|---|---|---|---|---|
| 2019/0309245 | A1* | 10/2019 | Shimagaki | C12M 25/04 |
| 2020/0354668 | A1 | 11/2020 | Sawyer et al. | |
| 2022/0396754 | A1* | 12/2022 | Castillo | C12M 23/34 |

* cited by examiner

Pressurized Perfusion Enabled Bio-Reactor 100
111
101
103
105
107
109

TOP VIEW

BOTTOM VIEW
DIMETRIC VIEW

FRONT VIEW

SECTION VIEW

DEVICES, SYSTEMS, AND METHODS RELATING TO PRESSURIZED PERFUSION-ENABLED BIO-REACTORS

CROSS-REFERENCE TO RELATED APPLICATIONS

This application is the 35 U.S.C. § 371 national stage application of PCT Application No. PCT/US2022/072390, filed May 18, 2022, which claims the benefit of and priority to U.S. Provisional Application Ser. No. 63/195,042 having the title "DEVICES, SYSTEMS, AND METHODS RELATING TO PRESSURIZED PERFUSION-ENABLED BIO-REACTORS," filed on May 30, 2021, the disclosure of both are incorporated herein in by reference in their entireties.

BACKGROUND

Transport of biological samples is paramount to clinical research, diagnostics, and clinical care of subjects in clinical and research settings.

Despite the necessity of sample transport, transport methods still remain relatively rudimentary. Current transport methods rely on cooling samples to slow metabolic, apoptotic, and autophagic processes or transporting samples in an unregulated static environment similar to a tissue culture incubator. While these methods are better than nothing and help maintain cell and tissue viability at the destination, cell and tissue viability at the destination remains poor—hindering the diagnostic, research, and clinical value of the transported samples.

Perfusion-enabled devices and systems have been previously described relating to perfusion using negative pressure and for the purpose of long-term tissue culture studies in basic research. For example, previous systems and methods utilizing negative pressure enabled long-term studies of biological samples through the incorporation of pressure-driven flow through a microgel bed, but the use of low-vacuum to produce the pressure gradient did not accommodate the use of desired gases and limited how compact the assembly could be made as it relates to tissue transport.

Accordingly, there is a need to address the aforementioned deficiencies and inadequacies and/or other items to provide for improved devices, systems, and methods for biological sample transport that retains a high level of sample viability at the transport destination.

SUMMARY

The present disclosure provides for devices, systems, and methods relating to pressurized perfusion enabled bio-reactor[s], in particular perfusion-enabled bioreactors, systems, and methods thereof pressurized with positive pressure (+).

The present disclosure provides for positive pressure perfusion-enabled bioreactors (e.g., vertical and horizontal orientations). In embodiments, positive pressure perfusion-enabled bioreactors can comprise a bioreactor having a central chamber bound by high pressure side (e.g., top in the vertical orientation) and a low pressure side (e.g., bottom in the vertical orientation) and one or more walls; and an interlocking cap and frame in the central chamber.

The cap can comprise a plurality of retrieval features arranged around a central cap aperture and extending upwards (e.g., in the vertical orientation) towards an opening of the bioreactor; and the frame can comprise a plurality of height offsets arranged around a central frame aperture and extending downwards (e.g., in the vertical orientation) towards the low pressure side (e.g., bottom) of the bioreactor in a direction opposite the retrieval features. The cap and frame are configured to interlock through an interference fit, forming an interlocked cap and frame, thereby aligning and forming a sample chamber in between the central frame aperture and the central cap aperture; and one or more membranes spanning the central frame aperture, the central cap aperture, or both.

In an aspect, positive pressure perfusion-enabled bioreactors as described herein can further comprise one or more inner seals separating one or more interlocked portions of the cap and the frame.

In an aspect, positive pressure perfusion-enabled bioreactors as described herein can further comprise one or more outer seals positioned in between the interlocked cap and frame and one or more outer walls of the bioreactor.

In an aspect, positive pressure perfusion-enabled bioreactors as described herein can further comprise a ventilation aperture in the one or more outer walls of the bioreactor below the one or more outer seals.

In an aspect, positive pressure perfusion-enabled bioreactors as described herein can further a top configured to seal the opening of the bioreactor opposite the bottom.

In an aspect, positive pressure perfusion-enabled bioreactors as described further comprise a top (e.g., in the vertical orientation) configured to receive fluid under positive pressure. In embodiments, the fluid is a gas or mixture of gases. In embodiments, the bioreactor can be a conical tissue culture tube, a well of a tissue culture plate, or another shape that is custom designed.

The present disclosure also provides for systems. In embodiments, described herein are a positive pressure perfusion-enabled bioreactor system, comprising a bioreactor as described herein and a support medium in the sample chamber as described herein. In embodiments, the support medium comprises hydrogel particles dispersed in a liquid cell growth medium.

In an aspect, systems as described herein further comprise a fluid feed chamber configured to hold fluid that is provided to the bioreactor under positive pressure and a bioreactor feed line to provide fluid from the fluid feed chamber to the bioreactor through the top of the bioreactor. In embodiments, systems as described herein further comprise a fluid feed line to provide fluid to the fluid feed chamber.

In an aspect, systems as described herein further comprise a valve operably connected with the fluid feed line to regulate fluid flow to the fluid feed chamber.

In an aspect, systems as described herein further comprise a system housing to hold and support the bioreactor and fluid feed chamber.

The present disclosure also provides for methods. In embodiments, methods as described herein comprise providing a bioreactor; seating a frame in an inner chamber of the bioreactor with height offsets extending towards the bioreactor bottom (e.g., low pressure side) (e.g., in the vertical orientation); providing a support medium into a chamber of the frame and on top of a membrane spanning a central aperture of the frame; placing a biological sample into support medium; providing a cap and interlocking the cap with the frame. In embodiments of methods as described herein, methods further comprise applying positive pressure to a side of the support medium opposite the bottom (e.g., in the vertical orientation) of the bioreactor. In embodiments, methods as described herein comprise sealing the chamber of the bioreactor with a top. In embodiments, methods as described herein comprise providing fluid under positive pressure to the chamber of the bioreactor.

The details of one or more embodiments of the present disclosure are set forth in the accompanying drawings and the description below. Other features, objects, and advantages of the present disclosure will be apparent from the description and drawings, and from the claims.

DESCRIPTION OF DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 2 is an embodiment of a pressurized perfusion-enabled bioreactor as described herein.

FIG. 3 is an exploded view of the embodiment of a pressurized perfusion-enabled bioreactor as shown in FIG. 2.

FIG. 8 is another cross-sectional view of the embodiment of FIG. 6.

FIG. 13 is a cross-sectional view of the embodiment of FIG. 12.

DETAILED DESCRIPTION

Figure 1A:
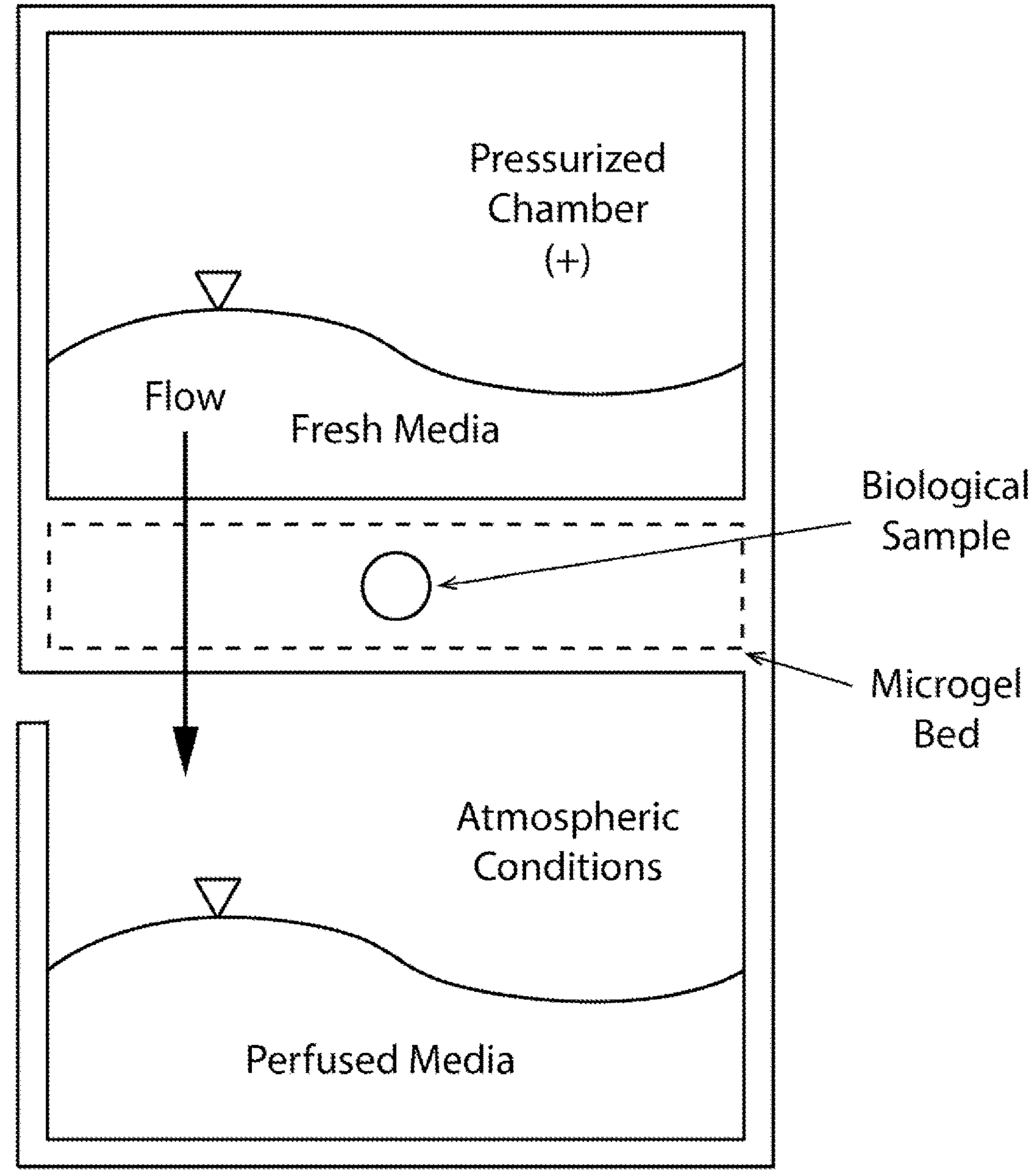
FIG. 1A is a cartoon schematic of pressurized (positive pressure) perfusion-enabled bioreactors as described herein having a vertical configuration.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, mechanical engineering, bio-medical engineering, material science, and the like, which are within the skill of the art.

The following examples are put forth so as to provide those of ordinary skill in the art with a complete disclosure and description of how to perform the methods and use the compositions, methods, and materials disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Definitions

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described herein.

Two events or entities are "associated" with one another, as that term is used herein, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

As used herein, the term "comparable" refers to two or more agents, entities, situations, sets of conditions, etc., that may not be identical to one another but that are sufficiently similar to permit comparison there between so that one skilled in the art will appreciate that conclusions can reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Those skilled in the art will appreciate that the term "composition", as used herein, can be used to refer to a discrete physical entity that comprises one or more specified components. In general, unless otherwise specified, a composition can be of any form—e.g., gas, gel, liquid, solid, etc.

As used herein, these terms, or grammatically comparable comparative terms "improved," "increased" or "reduced", indicate values that are relative to a baseline value or reference measurement. For example, in some embodiments, an assessed value achieved with an agent of interest may be "improved" relative to that obtained or expected in the absence of treatment or with a comparable reference agent or control. Alternatively, or additionally, in some embodiments, an assessed value achieved with an agent of interest may be "improved" relative to that obtained in the same subject or system under different conditions (e.g., prior to or after an event such as administration of an agent of interest), or in a different, comparable subject (e.g., in a comparable subject or system that differs from the subject or system of interest). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

As used herein, "sample" refers to one or more biological substances (preferable a mammalian cell or plurality of mammalian cells or tissue[s]) whose position can be transported and/or physiologically maintained using systems and methods as described herein.

Discussion

The present disclosure provides for devices, systems, and methods related to pressurized perfusion enabled-bioreactors, in particular those pressurized with positive pressure. The devices, systems, and methods can accommodate such a setup. In environments where gas levels could be monitored and controlled the low-vacuum design was not a hindrance, but there remain circumstances where a user would choose to pressurize the device with a desired gas to improve sample viability or study associated effects.

At least one distinction made between previous perfusion-enabled devices and systems and the disclosure is the incorporation of positive pressure in this device, which could be realized using external connections, integrated mechanical features (springs, bellows, membranes, pumps etc.), or through other means known in the art by the skilled artisan.

Devices, systems, and methods as described herein are capable of carrying out a wide variety of tasks due to the incorporation of positive pressure. As an example, in an atmospheric environment devices and systems as described herein could be pressurized with oxygen to improve biological sample viability and closely regulate the metabolic rate of enclosed cells. Additionally, devices and systems as described herein could accommodate drug infusion studies, 3D cell culture, shipment of biological samples, and micro-gel equilibration. Fabrication of devices and systems as described herein would likely involve injection molding of a clear plastic to accommodate observation of the media conditions but could be accomplished through other ways (additive manufacturing, for example). In other aspects, the addition of support media-retaining membranes (for example (heat-sealed membranes, such as dialysis membranes)) can improve reliability of devices and systems as described herein, and the inclusion of seals would allow for a relatively modular assembly. For sterility concerns, aspects of systems as described herein can be designed to be disposable (i.e., for single uses such as to degrade after a single use).

The positive pressure could be a range of values, and this does depend on the design of the system and the materials that it is made of. A range of pressures you could give would be about 3-15 psi, about 5 to 15 psi, about 5 to 10 psi, however this is not an exhaustive list, as these could change if the tube material and the membrane materials were stronger. For example, if the tube was thicker stronger plastic and the membrane was a stainless steel mesh, the pressures could be much higher, even potentially about 20 psi or more. In another example, the strength of the enclosure is one aspect to consider for pressurization, however the desired fluid flow rates through the support medium and around the biological samples is also a function of the pressure. As such, the pressure ranges that can be used with this device could vary greatly due to materials of construction and specifics of the sample.

In an aspect, the positive pressure perfusion-enabled bioreactor can have a vertical orientation (FIG. 1A) (e.g., a top and a bottom) or can have a horizontal orientation, where in each embodiment, there is a high pressure side and a low pressure side. In a vertical orientation (FIG. 1A), the top side is the high pressure side and the bottom side is the low pressure side. In the horizontal orientation (FIG. 1B) the high pressure side and low pressure side can be on either side. The vertical orientation and the horizontal orientation generally operate in a similar manner and include the same components are provided herein.

In general, the positive pressure perfusion-enabled bioreactor can include a bioreactor and an interlocking cap and frame. The bioreactor can have a central chamber bound by a high pressure side (e.g., a top side in a vertically oriented bioreactor) and a low pressure side (e.g., a bottom side opposite the top side in the vertically oriented bioreactor) and one or more walls and the interlocking cap and frame in the central chamber. The cap can include a plurality of retrieval features arranged around a central cap aperture and extending toward an opening at the high pressure side of the bioreactor. The frame can include a plurality of height offsets arranged around a central frame aperture and extending toward the low pressure side of the bioreactor in a direction opposite the retrieval features. The cap and frame can be configured to interlock through an interference fit, forming an interlocked cap and frame, thereby aligning and forming a sample chamber in between the central frame aperture and the central cap aperture. One or more membranes can span the central frame aperture, the central cap aperture, or both. Additional details are provided in the Examples and figures.

Having described aspects of the present disclosure generally, the following provides additional details. In certain aspects, systems as described herein can comprise a two-tube design comprising a perfusion-enabled bioreactor with a positive pressure design that can be used for shipping of tissues and cells. In certain aspects, systems can comprise a large tube in fluidic communication with the bioreactor (also described herein as a fluid feed tube or fluid feed chamber) that can be used as a ballast for the gas environment of choice (thereby eliminating the need for a portable incubator) and a second perfusion-enabled bioreactor with a specially designed framework (an interlocking cap and frame) that fixes the geometry in the perfusion tube. In further aspects, the framework can have one or more (two, in certain embodiments) membranes that can assist in containing a sample support medium should the reactors be shaken during transportation.

Devices and systems as described herein can comprise a frame. In certain aspects, the frame can be nested within a bioreactor as described herein. Frames as described herein can comprise a central aperture and plurality of height offsets extending orthogonally away from the central aperture. The height offsets serve several purposes, in particular (1) prevents media from flowing out of the effluent collection; (2) allows a certain volume of media to flow through the support media; and (3) prevents the inner seal[s], outer seal[s], or both from being pushed too far towards the bottom of the bioreactor by the user, which could punction or otherwise alter the fluid transport mechanics. In other aspects, the frame can comprise a membrane spanning the central aperture (membranes described in further detail below). In other aspects, the frame can be configured to interlock with caps as described herein through interference or threaded fits as known in the art.

The frame can be made out of any biocompatible plastic or other materials or can be made out of metal. As for manufacturing methods, the frame has been designed for injection molding, however it is not required to be made this way. Other manufacturing methods are definitely possible. 3D printing, milling, casting, and the like.

Devices and systems as described herein can comprise a cap. In certain aspects, the cap can be nested within a bioreactor as described herein. Caps as described herein can comprise a central aperture and plurality of retrieval features extending orthogonally away from the central aperture. The retrieval features allow for easy retrieval from the bioreactor by the user. In other aspects, the cap can optionally comprise a membrane spanning the central aperture (membranes described in further detail below). In other aspects, the frame can be configured to interlock with caps as described herein through interference or threaded fits as known in the art, wherein the interlocking arrangement provides that the retrieval features of the cap and height offsets of the frame extend in opposite directions and whereby a sample chamber is formed by in the interlock and bounded on opposite sides by the central apertures of the cap and the frame (or membrane[s] spanning the respective central apertures).

This item could be made out of any biocompatible plastic or other materials. It could be made out of metal if one really wanted to. As for manufacturing methods, it has been designed for injection molding, however it is not required to be made this way. Other manufacturing methods are definitely possible. 3D printing, milling, casting, and the like.

Devices and systems as described herein can comprise one or more inner seals between one or more abutting portions of the interlocked cap and frame, respectively. Such seals can be rubber o-rings, custom made silicone O-rings, biocompatible sealing greases, interference fit with plastic (no elastomer). This could also be plastic welded (fused together) if desired. As the skilled artisan would understand, such inner seals prevent leakage of fluid between the interlocked cap and frame.

Devices and systems as described herein can comprise one or more outer seals between the interlocked cap and frame and the inner surfaces of the one or more outer walls of the bioreactor, respectively. Such seals can be rubber o-rings, custom made silicone O-rings, biocompatible sealing greases, interference fit with plastic (no elastomer). This could also be plastic welded (fused together) if desired. As the skilled artisan would understand, such outer seals prevent leakage of fluid between the interlocked cap and frame assembly and the inner surfaces of the one or more outer walls of the bioreactor.

Devices and systems as described herein can comprise one or more bioreactors in which caps, frames, or interlocked caps and frames can be situated. In an aspect, the bioreactors are conical tissue culture tubes (such as 5 mL, 10 mL, 25 mL, 50 mL, and the like). In an aspect, the bioreactors as described herein are a well of a tissue culture plate (for example a 6-well, 24-well, 48-well, 96-well, or 384-well tissue culture plate). In an aspect, the bioreactors have a bottom surface (opposite an opposing top surface) that can be flat, tapered, concave, or convex. In embodiments of bioreactors as described herein of conical tissue culture tubes with tapered bottom surfaces, such bioreactors can further comprise a "skirt" extending downward from the outer wall[s] (e.g., perpendicular to the bottom or substantially perpendicular to the bottom) toward and flush with the bottom-most surface of the bottom so as to physically stabilize the tube when placed bottom side-down on a flat surface.

Bioreactors as described herein can further comprise a top (that opposes the bottom), such as a top that screws onto a conical tissue culture tube or a cover for a well plate. Tops of bioreactors as described herein can be configured to receive fluid (such as the feed gas) from the feed gas chamber, for example through a valve connected to plastic tubing via an interference fit. A similar arrangement can be configured for the horizontal orientation of the bioreactor.

In embodiments, the one or more outer walls of the bioreactor can comprise one or more ventilation apertures configured to be placed in between the bottom surface of the bioreactor and the culture chamber formed by the interlocking cap and frame. The one or more ventilation apertures (1) allow gases to escape from the bioreactor; (2) prevents pressure equilibrium; and (3) prevents the biological sample/support medium from being ejected from the device when the top of the device is opened.

Systems as described herein can further comprise a transport housing configured to support and physically stabilize (i.e., prevent translational movement or unwanted vibrations) a bioreactor as described herein, a feed gas chamber as described herein, or both. Transport housings as described herein can also be configured to fix in place other aspect of systems as described herein, for example fluid supply lines, valves, and the like.

Devices and systems as described herein can comprise one or more support membranes spanning the central aperture of the cap, frame, or both.

In an aspect, the one or more support membranes comprise a heat-sealed membrane. In particular, the one or more support membranes comprise a heat-sealed dialysis membrane, custom made silicone O-rings, biocompatible sealing greases, interference fit with plastic (no elastomer). This could also be plastic welded (fused together) if desired. Other microporous membranes not for dialysis could also be used.

This could be anything from vacuum filtration membranes used for chemistry to even metal meshes used for straining fuels. The pores in the membrane need to be nominally smaller than the size of the LLS particles, which is about 70 μm in characteristic diameter. The particle size could also change as well.

Adhesion of the membrane or other suitable support material for this case could be performed with heat sealing, biocompatible adhesives like superglue or certain silicones. This is a common procedure that a skilled artisan in the field of medical devices should be able to understand.

In an embodiment, one membrane is present on the frame. In another embodiment, one membrane is present on the frame, and a second membrane is present on the cap such that when the cap and frame are interlocked, a sample chamber is formed that is bound on opposite sides by the two support membranes.

As the skilled artisan would immediately envisage, the input gas (i.e., feed gas) to be provided to the perfusion-enabled bioreactor[s] as described herein under positive pressure will depend on the application.

In embodiments of devices and systems as described herein, an input gas (i.e., feed gas) is provided to a bioreactor under positive pressure from a feed gas chamber in fluidic communication with the bioreactor (such as through plastic tubing connected by interference-fit connectors). The input gas (i.e., feed gas) can be provided to the feed gas chamber from a feed gas source via a supply line, for example through plastic tubing connected by interference-fit connectors. The supply line can comprise one or more one-way valves that allow gas input but prevent gas efflux from the feed gas chamber. Such valves can also be adjustable by the user to adjust supply variables, such as supply volume, pressure, and the like.

In embodiments, the input gas can comprise one or more gasses (alone or admixed) typically found in the atmosphere (such as oxygen, nitrogen, or carbon dioxide). In embodiments, the humidity of the input gas (and/or devices or systems) can be adjusted to a set range and/or a set temperature, for example to values typically found in tissue culture incubators of basic research and clinical laboratories.

In certain embodiments, the input gas can comprise about or at least 90% oxygen ($O_2$). The input gas could be whatever is necessary for the culture and health of the biological samples being used here. For many aspects, high $O_2$ levels (90% or so) is beneficial, however this may not be the case for other samples, and the skilled artisan could vary oxygen or gas levels according to the biological sample in the support material, the support material, or both. Therefore, the input gas is not limited to this level of oxygen or oxygen at all if that was required. It is important to note that the use of positive pressure allows for the use of whatever gas mixture is desired without having to worry about what gasses are present in the atmosphere surrounding the samples.

In certain aspects, bio-manipulators as described herein can be used in conjunction with biological samples and a support medium.

In embodiments, and without intending to be limiting, the support medium can comprise agar, gelatin, Matrigel®, or other such semi-solid support mediums known in the art of tissue culture. Additional examples include agarose, gelatins or various types, solidified collagen, liquid like solids (as described herein). Any support material capable of perfusion through its bulk under a pressure gradient could be used here. Chopped up seaweed with plankton interspersed would work if that was the desired sample.

In an embodiment, the support medium can be a liquid-like solid (LLS) three-dimensional (3D) cell growth medium, as further described below.

Liquid-like solid (LLS) three-dimensional (3D) cell growth medium for use in with the disclosed bio-manipulator system is disclosed in WO2016182969A1 by Sawyer et al., which is incorporated by reference in its entirety for the description of how to make and uses this LLS medium.

Briefly, the 3D cell growth medium may comprise hydrogel particles dispersed in a liquid cell growth medium. Any suitable liquid cell growth medium may be used; a particular liquid cell growth medium may be chosen depending on the types of cells which are to be placed within the 3D cell growth medium. For example, suitable cell growth medium may be human cell growth medium, murine cell growth medium, bovine cell growth medium or any other suitable cell growth medium. Depending on the particular embodiment, hydrogel particles and liquid cell growth medium may be combined in any suitable combination. For example, in some embodiments, a 3D cell growth medium comprises approximately 0.5% to 10% polymer by weight.

In accordance with some embodiments, the hydrogel particles may be made from a bio-compatible polymer.

The hydrogel particles may swell with the liquid growth medium to form a granular gel material. Depending on the particular embodiment, the swollen hydrogel particles may have a characteristic size at the micron or submicron scales. For example, in some embodiments, the swollen hydrogel particles may have a size between about 0.1 μm and 200 μm. Furthermore, a 3D cell growth medium may have any suitable combination of mechanical properties, and in some embodiments, the mechanical properties may be tuned via the relative concentration of hydrogel particles and liquid cell growth medium. For example, a higher concentration of hydrogel particles may result in a 3D growth medium having a higher elastic modulus and/or a higher yield stress.

According to some embodiments, the 3D cell growth medium may be made from materials such that the granular gel material undergoes a temporary phase change due to an applied stress (e.g. a thixotropic or "yield stress" material). Such materials may be solids or in some other phase in which they retain their shape under applied stresses at levels below their yield stress. At applied stresses exceeding the yield stress, these materials may become fluids or in some other more malleable phase in which they may alter their shape. When the applied stress is removed, yield stress materials may become solid again. Stress may be applied to such materials in any suitable way. For example, energy may be added to such materials to create a phase change. The energy may be in any suitable form, including mechanical, electrical, radiant, or photonic, etc.

Regardless of how cells are placed in the medium, the yield stress of the yield stress material may be large enough to prevent yielding due to gravitational and/or diffusional forces exerted by the cells such that the position of the cells within the 3D growth medium may remain substantially constant over time. As described in more detail below, placement and/or retrieval of groups of cells may be done manually or automatically.

A yield stress material as described herein may have any suitable mechanical properties. For example, in some embodiments, a yield stress material may have an elastic modulus between approximately 1 Pa and 10000 Pa when in a solid phase or other phase in which the material retains its shape under applied stresses at levels below the yield stress. In some embodiments, the yield stress required to transform a yield stress material to a fluid-like phase may be between approximately 1 Pa and 10000 Pa. In some embodiments, the yield stress may be on the order of 10 Pa, such as 10 Pa +/−25%. When transformed to a fluid-like phase, a yield stress material may have a viscosity between approximately 1 Pa s and 10,000 Pa s. However, it should be understood that other values for the elastic modulus, yield stress, and/or viscosity of a yield stress material are also possible, as the present disclosure is not so limited.

A group of cells may be placed in a 3D growth medium made from a yield stress material via any suitable method. For example, in some embodiments, cells may be injected or otherwise placed at a particular location within the 3D growth medium with a syringe, pipette, or other suitable placement or injection device. In some embodiments an array of automated cell dispensers may be used to inject multiple cell samples into a container of 3D growth medium. Movement of the tip of a placement device through the 3D growth medium may impart a sufficient amount of energy into a region around the tip to cause yielding such that the placement tool may be easily moved to any location within the 3D growth medium. In some instances, a pressure applied by a placement tool to deposit a group of cells within the 3D growth medium may also be sufficient to cause yielding such that the 3D growth medium flows to accommodate the group of cells. Movement of a placement tool may be performed manually (e.g., "by hand") or may performed by a machine or any other suitable mechanism.

In some embodiments, multiple independent groups of cells may be placed within a single volume of a 3D cell growth medium. For example, a volume of 3D cell growth medium may be large enough to accommodate at least 2, at least 5, at least 10, at least 20, at least 50, at least 100, at least 1000, or any other suitable number of independent groups of cells. Alternatively, a volume of 3D cell growth medium may only have one group of cells. Furthermore, it should be understood that a group of cells may comprise any suitable number of cells, and that the cells may of one or more different types.

Depending on the particular embodiment, groups of cells may be placed within a 3D cell growth medium according to any suitable shape, geometry, and/or pattern. For example, independent groups of cells may be deposited as spheroids, and the spheroids may be arranged on a 3D grid, or any other suitable 3D pattern. The independent spheroids may all comprise approximately the same number of cells and be approximately the same size, or alternatively different spheroids may have different numbers of cells and different sizes. In some embodiments, cells may be arranged in shapes such as embryoid or organoid bodies, tubes, cylinders, toroids, hierarchically branched vessel networks, high aspect ratio objects, thin closed shells, or other complex shapes which may correspond to geometries of tissues, vessels or other biological structures.

According to some embodiments, a 3D cell growth medium made from a yield stress material may enable 3D printing of cells to form a desired pattern in three dimensions. For example, a computer-controlled injector tip may trace out a spatial path within a 3D cell growth medium and inject cells at locations along the path to form a desired 3D pattern or shape. Movement of the injector tip through the 3D cell growth medium may impart sufficient mechanical energy to cause yielding in a region around the injector tip to allow the injector tip to easily move through the 3D cell growth medium, and also to accommodate injection of cells.

After injection, the 3D cell growth medium may transform back into a solid-like phase to support the printed cells and maintain the printed geometry. However, it should be understood that 3D printing techniques are not required to use a 3D growth medium as described herein.

According to some embodiments, a 3D cell growth medium may be prepared by dispersing hydrogel particles in a liquid cell growth medium. The hydrogel particles may be mixed with the liquid cell growth medium using a centrifugal mixer, a shaker, or any other suitable mixing device. During mixing, the hydrogel particles may swell with the liquid cell growth medium to form a material which is substantially solid when an applied shear stress is below a yield stress, as discussed above. After mixing, entrained air or gas bubbles introduced during the mixing process may be removed via centrifugation, agitation, or any other suitable method to remove bubbles from 3D cell growth medium.

In some embodiments, preparation of a 3D cell growth medium may also involve buffering to adjust the pH of a hydrogel particle and liquid cell growth medium mixture to a desired value. For example, some hydrogel particles may be made from polymers having a predominantly negative charge which may cause a cell growth medium to be overly acidic (have a pH which is below a desired value). The pH of the cell growth medium may be adjusted by adding a strong base to neutralize the acid and raise the pH to reach the desired value. Alternatively, a mixture may have a pH that is higher than a desired value; the pH of such a mixture may be lowered by adding a strong acid.

According to some embodiments, the desired pH value may be in the range of about 7.0 to 7.4, or, in some embodiments 7.2 to 7.6, or any other suitable pH value which may, or may not, correspond to in vivo conditions. The pH value, for example may be approximately 7.4. In some embodiments, the pH may be adjusted once the dissolved $CO_2$ levels are adjusted to a desired value, such as approximately 5%.

Yield stress can be measured by performing a strain rate sweep in which the stress is measured at many constant strain rates. Yield stress can be determined by fitting these data to a classic Herschel-Bulkley model ($\sigma=\sigma_y+k\dot{\gamma}^n$). (b) To determine the elastic and viscous moduli of non-yielded LLS media, frequency sweeps at 1% strain can be performed. The elastic and viscous moduli remain flat and separated over a wide range of frequency, behaving like a Kelvin-Voigt linear solid with damping. Together, these rheological properties demonstrate that a smooth transition between solid and liquid phases occurs with granular microgels, facilitating their use as a 3D support matrix for cell printing, culturing, and assaying.

An example of a hydrogel with which some embodiments may operate is a carbomer polymer, such as Carbopol®. Carbomer polymers may be polyelectrolytic and may comprise deformable microgel particles. Carbomer polymers are particulate, high-molecular-weight crosslinked polymers of acrylic acid with molecular weights of up to 3-4 billion Daltons. Carbomer polymers may also comprise co-polymers of acrylic acid and other aqueous monomers and polymers such as poly-ethylene-glycol.

While acrylic acid is a common primary monomer used to form polyacrylic acid the term is not limited thereto but includes generally all α-β unsaturated monomers with carboxylic pendant groups or anhydrides of dicarboxylic acids and processing aids as described in U.S. Pat. No. 5,349,030. Other useful carboxyl containing polymers are described in U.S. Pat. No. 3,940,351, directed to polymers of unsaturated carboxylic acid and at least one alkyl acrylic or methacrylic ester where the alkyl group contains 10 to 30 carbon atoms, and U.S. Pat. Nos. 5,034,486; 5,034,487; and 5,034,488; which are directed to maleic anhydride copolymers with vinyl ethers. Other types of such copolymers are described in U.S. Pat. No. 4,062,817 wherein the polymers described in U.S. Pat. No. 3,940,351 contain additionally another alkyl acrylic or methacrylic ester and the alkyl groups contain 1 to 8 carbon atoms. Carboxylic polymers and copolymers such as those of acrylic acid and methacrylic acid also may be cross-linked with polyfunctional materials as divinyl benzene, unsaturated diesters and the like, as is disclosed in U.S. Pat. Nos. 2,340,110; 2,340,111; and 2,533,635. The disclosures of all of these U.S. Patents are hereby incorporated herein by reference for their discussion of carboxylic polymers and copolymers that, when used in polyacrylic acids, form yield stress materials as otherwise disclosed herein. Specific types of cross-linked polyacrylic acids include carbomer homopolymer, carbomer copolymer and carbomer interpolymer monographs in the U.S. Pharmocopia 23 NR 18, and Carbomer and C10-30 alkylacrylate crosspolymer, acrylates crosspolymers as described in PCPC International Cosmetic Ingredient Dictionary & Handbook, 12th Edition (2008).

Carbomer polymer dispersions are acidic with a pH of approximately 3. When neutralized to a pH of 6-10, the particles swell dramatically. The addition of salts to swelled Carbomer can reduce the particle size and strongly influence their rheological properties. Swelled Carbomers are nearly refractive index matched to solvents like water and ethanol, making them optically clear. The original synthetic powdered Carbomer was trademarked as Carbopol® and commercialized in 1958 by BF Goodrich (now known as Lubrizol), though Carbomers are commercially available in a multitude of different formulations.

Hydrogels may include packed microgels—microscopic gel particles, ~5 μm in diameter, made from crosslinked polymer. The yield stress of Carbopol® is controlled by water content. Carbopol® yield stress can be varied between roughly 1-1000 Pa. Thus, both materials can be tuned to span the stress levels that cells typically generate. As discussed above, while materials may have yield stresses in a range of 1-1000 Pa, in some embodiments it may be advantageous to use yield stress materials having yield stresses in a range of 1-100 Pa or 10-100 Pa. In addition, some such materials may have thixotropic times less than 2.5, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

Yield stresses of less than 100 pascals are advantageous as they prevent the formation of unwanted crevasses in the 3D culture medium that detrimentally affects flow of fluid (and nutrient delivery/retrieval) throughout the material. Additionally, yield stresses in this range have advantages for the culture of cells, such as efficient waste retrieval and the ability of cells to expand in their environment without being unnecessarily constrained.

Growth medium (for example liquid medium) compositions as known in the art, that can be employed in addition to the 3D culture medium as described herein, must be considered from two perspectives relating to the desired tissue and/or cells that are to be utilized in devices and systems as described herein: basic nutrients (sugars, amino acids, and the like) and growth factors/cytokines. Examples of common growth medium compositions include those based on media such as Dulbecco's Modified Eagle Medium (DMEM) that can be supplemented with other components, such as non-essential amino acids, antibiotics or antibiotic cocktails (for example penicillin-streptomycin), and nutrients (such as those stemming from fetal bovine serum or other sources). The skilled artisan would understand that the specific growth medium to be employed in systems and methods as described herein will be dependent on the biological samples utilized and could tailor the growth medium accordingly based on their level of ordinary skill and knowledge in the art.

In embodiments, biological samples as described herein can be tissues or tissue biopsies of varying size from a subject (up to 10 mm in any given physical dimension) or even single cells or a plurality of cells.

In embodiments and without intending to be limiting, subjects, tissues, or cells as described herein can be mammalian in origin, in particular being derived from humans (Homo sapiens), rats (Rattus norvegicus, for example), or mice (Mus musculus, for example).

In embodiments, the biological samples can be placed in the support medium of devices, systems, and methods as described herein using three-dimensional (3D) printing and associated 3D printers suitable for placing biological samples.

A variety of different cells can be applied to the 3D growth medium of the disclosed systems. As the skilled artisan would envisage, cells as described herein can be mammalian cells with an origin of any germ layer (mesodermal, endodermal, ectodermal, or placental).

In some embodiments, these can be normal human cells or human tumor cells. The cells may be a homogeneous suspension or a mixture of cell types. The different cell types may be seeded onto and/or into the support medium sequentially, together, or after an initial suspension is allowed to attach and proliferate (for example, endothelial cells, followed by liver cells). Cells can be obtained from cell culture or biopsy. Cells can be of one or more types, either differentiated cells, such as endothelial cells or parenchymal cells, including nerve cells, or undifferentiated cells, such as stem cells or embryonic cells. In one embodiment, the medium is seeded with a mixture of cells including endothelial cells, or with totipotent/pluripotent stem cells which can differentiate into cells including endothelial cells, which will form "blood vessels", and at least one type of parenchymal cells, such as hepatocytes, pancreatic cells, or other organ cells.

Cells can be cultured initially and then used for screening of compounds for toxicity. Cells can also be used for screening of compounds having a desired effect. For example, endothelial cells can be used to screen compounds which inhibit angiogenesis. Tumor cells can be used to screen compounds for anti-tumor activity. Cells expressing certain ligands or receptors can be used to screen for compounds binding to the ligands or activating the receptors. Stem cells can be seeded, alone or with other types of cells. Cells can be seeded initially, then a second set of cells introduced after the initial bioreactor tissue is established, for example, tumor cells that grow in the environment of liver tissue. The tumor cells can be studied for tumor cell behaviors or molecular events can be visualized during tumor cell growth. Cells can be modified prior to or subsequent to introduction into the apparatus. Cells can be primary tumor cells from patients for diagnostic and prognostic testing. The tumor cells can be assessed for sensitivity to an agent or gene therapy. Tumor cell sensitivity to an agent or gene therapy can be linked to liver metabolism of set agent or gene therapy. Cells can be stem or progenitor cells and the stem or progenitor cells be induced to differentiate by the mature tissue. Mature cells can be induced to replicate by manipulation of the flow rates or medium components in the system.

Tissues as described herein can be tissues or tissue biopsies up to 10 mm in size (in any physical dimension—width, length, height, circumference, diameter, etc.). Tissues as described herein can be derived from a variety of sources, including ex vivo biopsies or dissections, or even derivation from tissue-cultured stem cells (such as embryonic stem cells or induced pluripotent stem cells) exposed to growth differentiation factors as known in the art in order to produce a desired differentiated tissue.

In embodiments, tissues as described herein comprise pancreatic biopsies from a mammalian subject (such as a human, mouse, or rat). Other tissues can be liver, brain, kidney, lung, epidermis, muscle, intestinal tissue, and the like, although these representative examples are not intended to be limiting. Furthermore, the tissues do not need to come from mammalian subjects.

Regarding the size of the tissue biopsies, the upper limit is set by the inner volume of the bioreactor, and sizes can be scaled up and down. That said there are limitations set by diffusion of molecules in cultures without vasculature—this is fairly commonly understood for those in the field of 3D culture.

The tissue size could be larger if it was a very porous tissue that allowed for perfusion of media through it. Similarly, the maximum size would have to be smaller if it was a very dense tissue and perfusion through it is not very efficient.

Without intending to be limiting, systems and methods as described herein have many different applications, such as assisting with the identification of markers of disease; assessing efficacy of anti-cancer therapeutics; testing gene therapy vectors; drug development; screening; studies of cells, especially stem cells; studies on biotransformation, clearance, metabolism, and activation of xenobiotics; studies on bioavailability and transport of chemical agents across epithelial layers; studies on bioavailability and transport of biological agents across epithelial layers; studies on transport of biological or chemical agents across the blood-brain barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratinogenicity of chemical agents; studies on genotoxicity, carcinogenicity, and mutagenicity of chemical agents; detection of infectious biological agents and biological weapons; detection of harmful chemical agents and chemical weapons; studies on infectious diseases; studies on the efficacy of chemical agents to treat disease; studies on the efficacy of biological agents to treat disease; studies on the optimal dose range of agents to treat disease; prediction of the response of organs in vivo to biological agents; prediction of the pharmacokinetics of chemical or biological agents; prediction of the pharmacodynamics of chemical or biological agents; studies concerning the impact of genetic content on response to agents; filter or porous material below microscale tissue may be chosen or constructed so as bind denatured, single-stranded DNA; studies on gene transcription in response to chemical or biological agents; studies on protein expression in response to chemical or biological agents; studies on changes in metabolism in response to chemical or biological agents; prediction of agent impact through database systems and associated models; prediction of agent impact through expert systems; and prediction of agent impact through structure-based models.

In additional applications of devices, systems, and methods as described herein include the transport of biological samples embedded in the support medium from a first physical location (laboratory, clinic, operating room, etc) to a second physical location (laboratory, clinic, operating room, etc).

A number of embodiments of the present disclosure have been described. Nevertheless, it will be understood that various modifications may be made without departing from the spirit and scope of the present disclosure. Accordingly, other embodiments are within the scope of the following claims.

In addition, the following embodiments and features can be incorporated into one or more aspects or embodiments as provided herein. The following are provided to illustrate additional features that can be incorporated together with embodiments provided above and herein as well as with one or more of each other. The present disclosure is not limited to each feature independently, rather various combinations of one or more of these features with one or more of the features disclosed above and herein in contemplated.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Figure 1B:
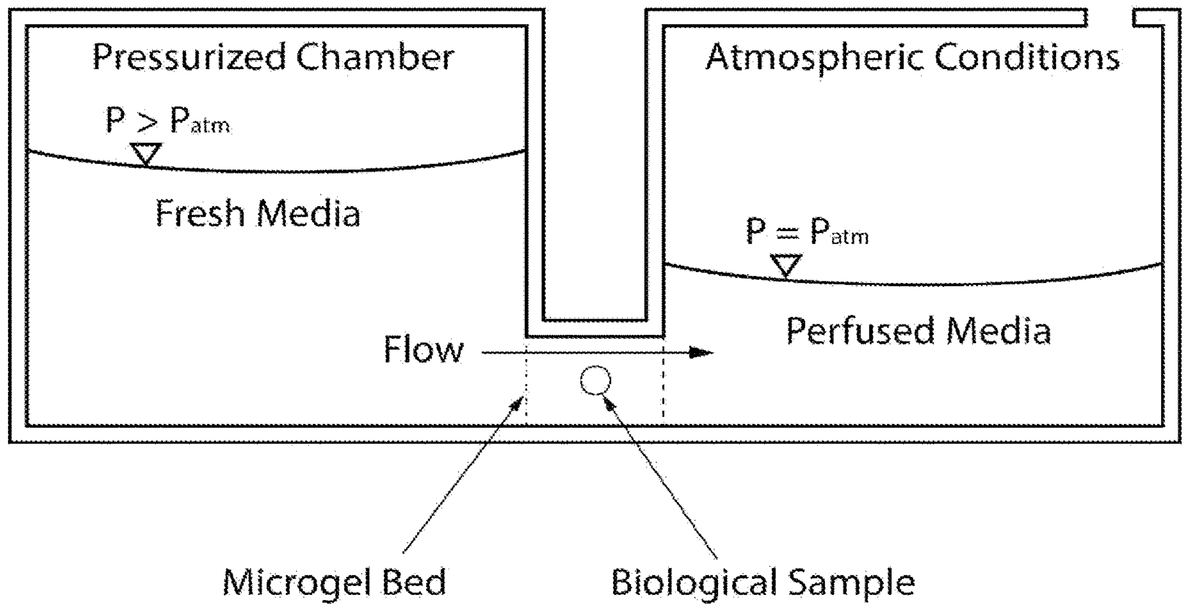
FIG. 1B is a cartoon schematic of pressurized (positive pressure) perfusion-enabled bioreactors as described herein having a horizontal configuration.

FIG. 1A is a cartoon schematic of pressurized (positive pressure) perfusion-enabled bioreactors as described herein having a vertical configuration. As shown in FIG. 1A, a biological sample lies in a support medium (a microgel bed according to the embodiment of FIG. 1A). A pressurized chamber drives fluid flow (fresh culture/growth media and or gasses) through the support media, to the tissue and exiting out of the support media. Similarly, FIG. 1B is a cartoon schematic of pressurized (positive pressure) perfusion-enabled bioreactors as described herein having a horizontal configuration. While FIG. 1B illustrates a pressurized (positive pressure) perfusion-enabled bioreactor has a horizontal configuration, FIG. 1B illustrates a pressurized chamber that drives fluid flow (fresh culture/growth media and or gasses) through the support media, to the tissue and exiting out of the support media.

Example 2

Figure 2:
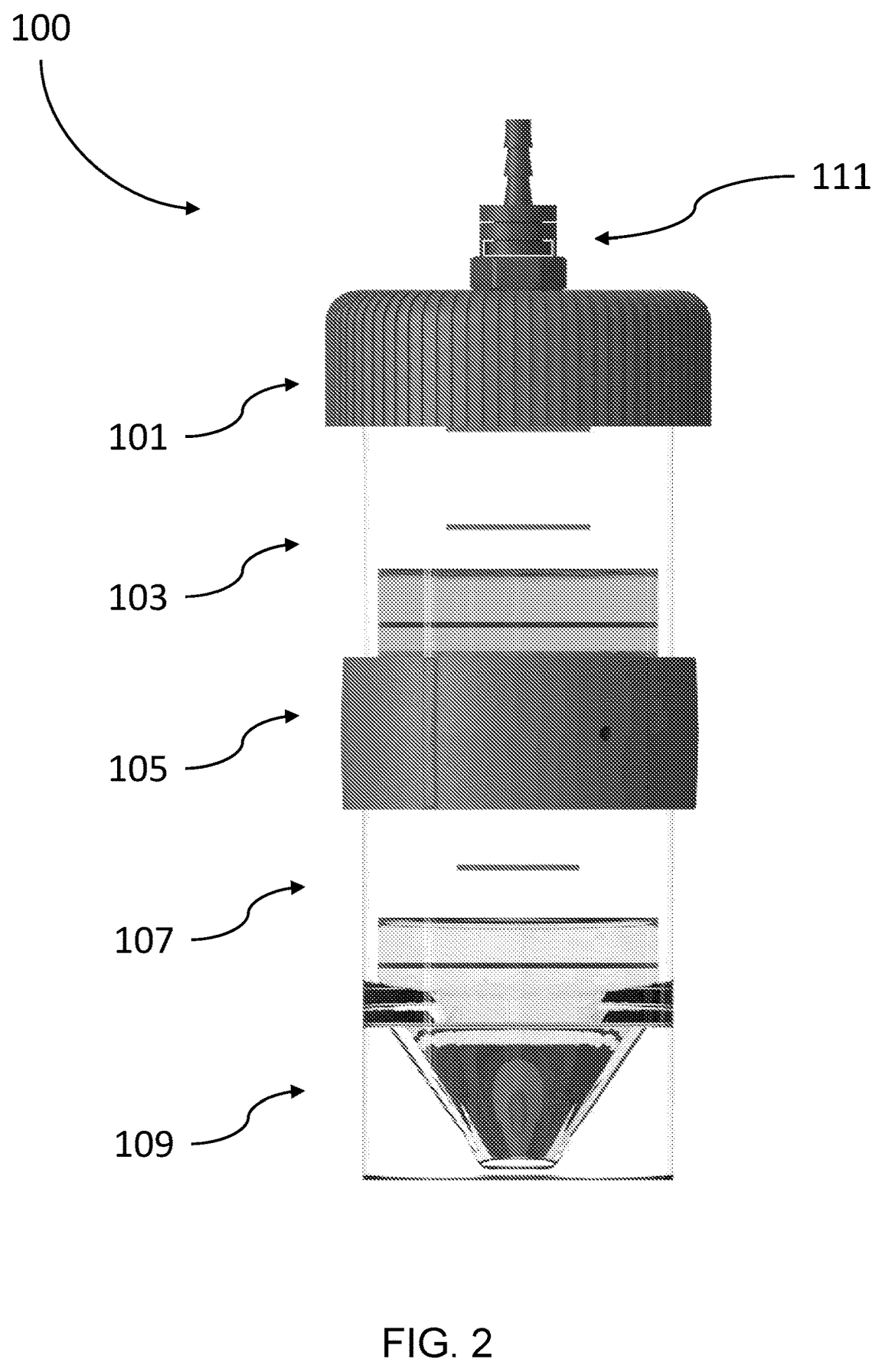
Figure 3:
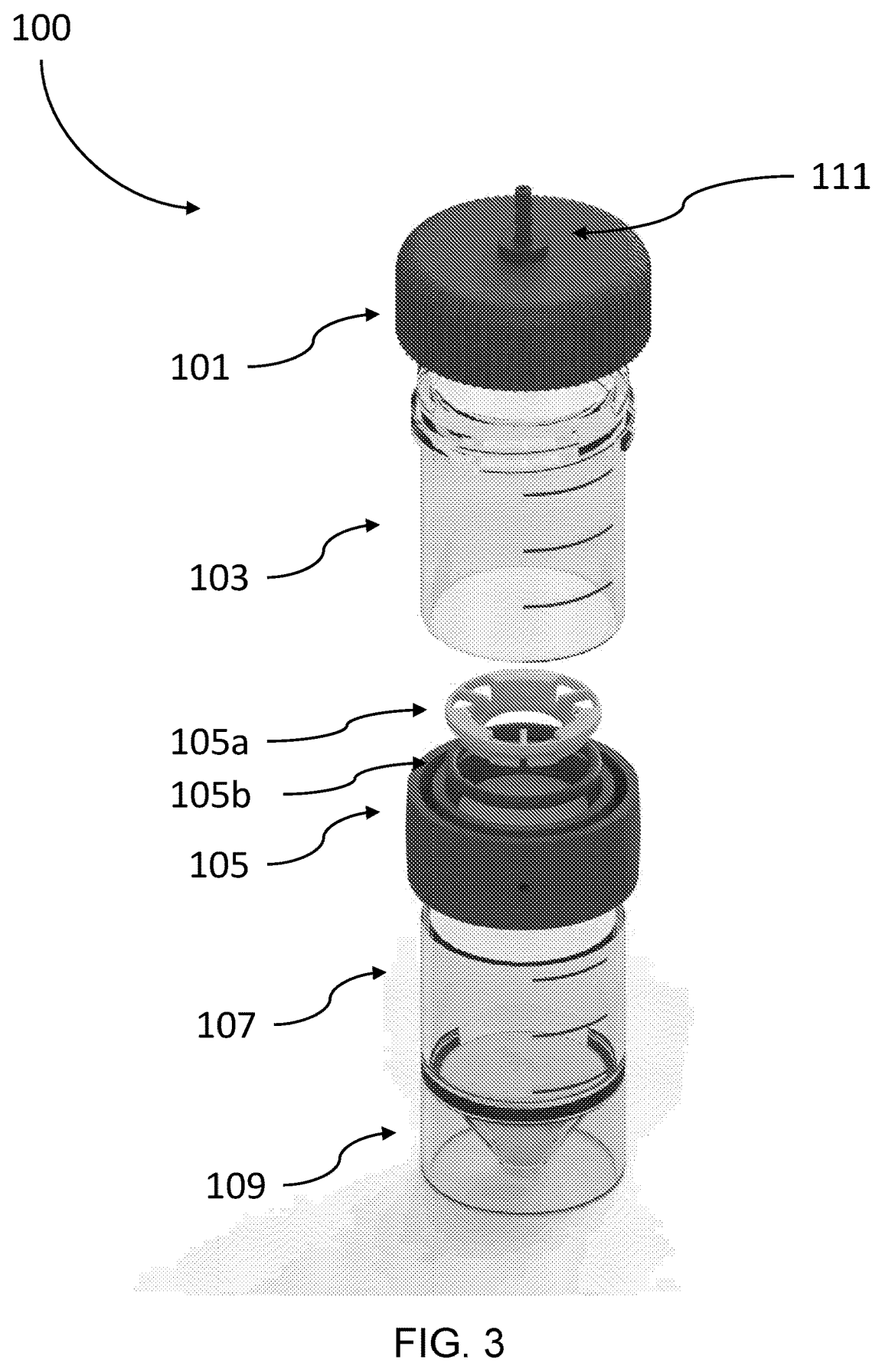

FIGS. 2-3 show an embodiment of a bioreactor 100 (and exploded view, FIG. 3) as described herein.

As shown in FIG. 2, a bioreactor 100 can be a conical tissue culture tube with a frame or frame assembly 105 bisecting the inner chamber (or volume) of the bioreactor. The top half 103 comprises fresh growth media under pressure (such as positive pressure) that is pushed through the frame 105 (comprising a support media) into the bottom half 107 where effluent is collected. A top 101 seals the bioreactor from the external environment (by an interference or threaded fit) and contains a connector 111 to receive plastic tubing through which pressurized gas is passed to the bioreactor. A skirt 109 extends downwards towards the tapered bottom (and continuous with the outer wall[s]) for placement stability.

Additional details of the frame/frame assembly 105 can be seen in the exploded view of FIG. 3, showing a cap 105*a* with a central aperture and an inner seal 105*b* that sits between the cap 105*a* and frame 105.

It is further noted that while aspects of the embodiment of the bioreactor 100 are depicted with annular and/or circular cross-sectional features (viewing down a longitudinal axis from top to bottom), such annular and/or circular geometry is not limiting.

Example 3

Figure 4:
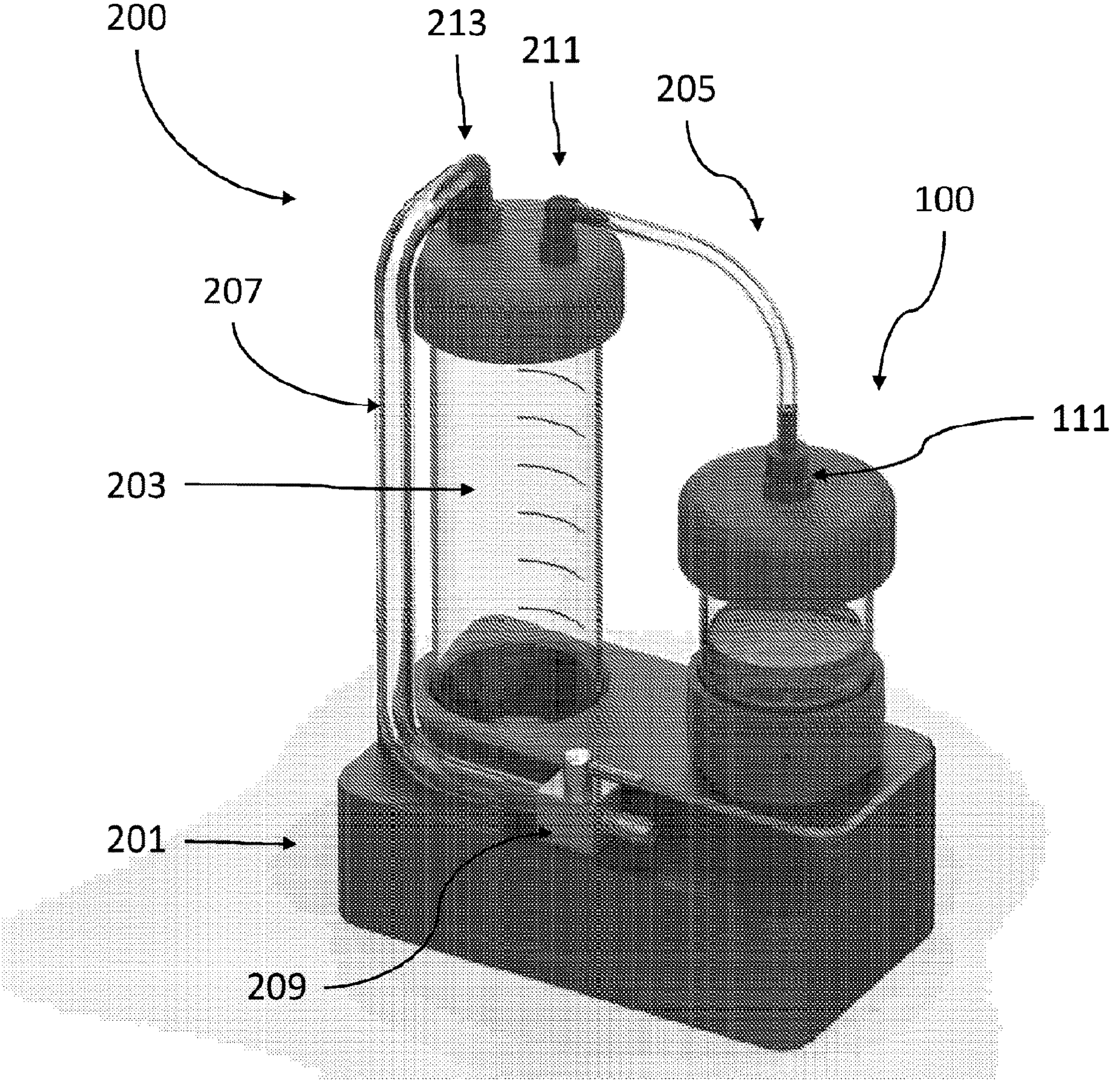
FIG. 4 is an embodiment of a pressurized perfusion-enabled bioreactor system as described herein, incorporating the embodiment of the pressurized perfusion-enabled bioreactor of FIG. 2.
Figure 5:
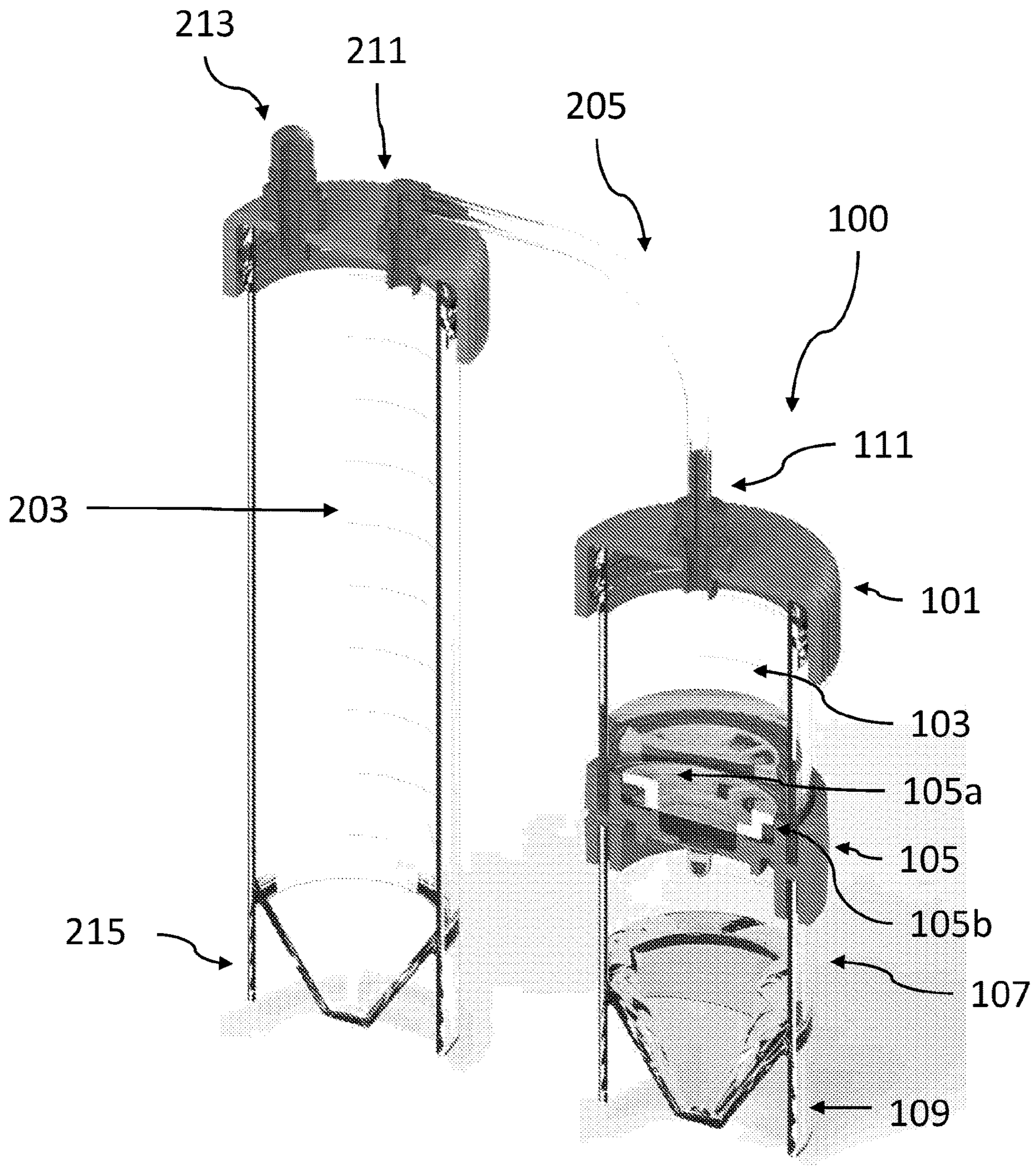
FIG. 5 is a cross-sectional view of an embodiment of a pressurized perfusion-enabled bioreactor system as described herein, in particular showing the bioreactor and fluid feed chamber with embodiments of associated inputs, outputs, and fluid connections.
Figure 6:
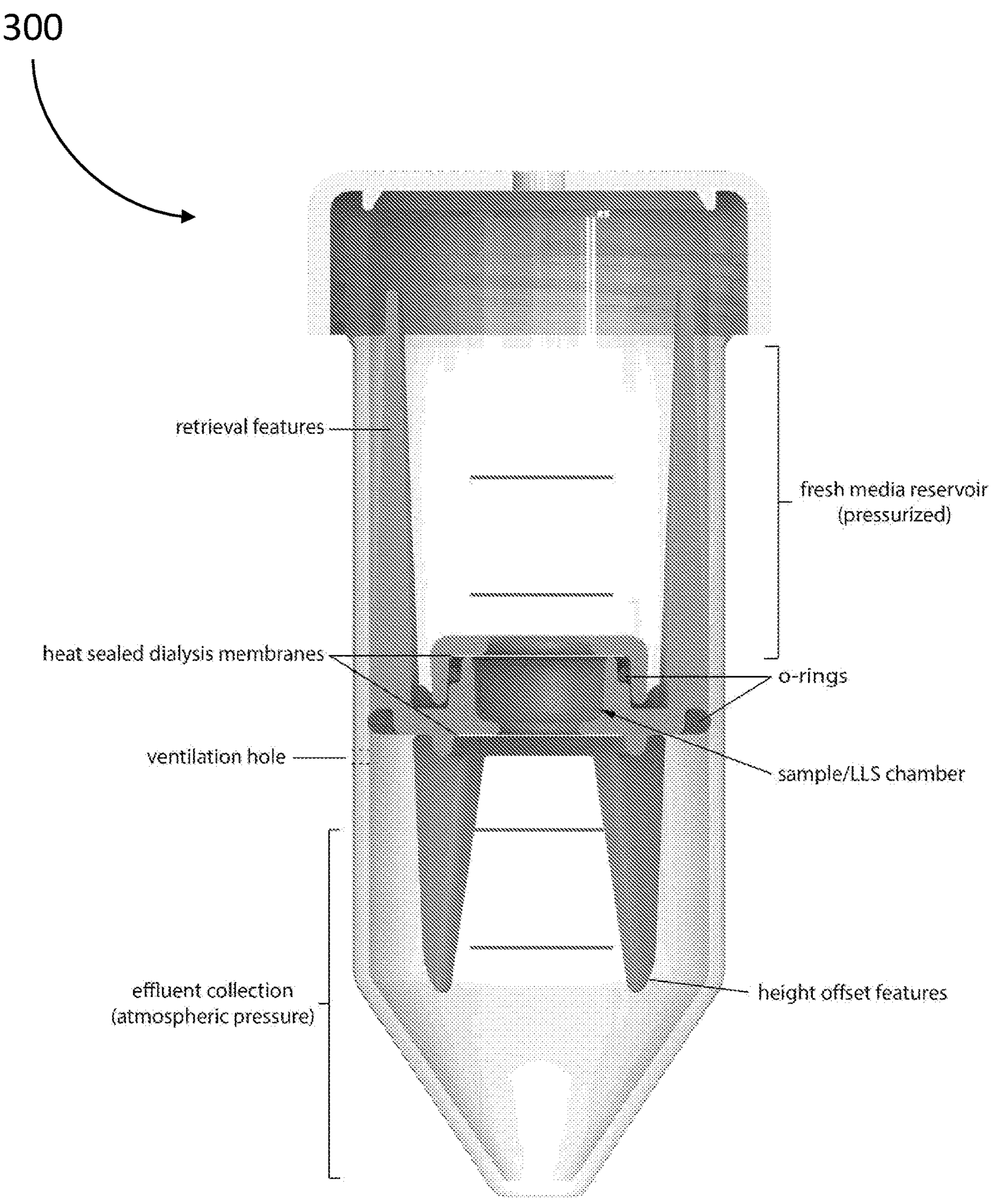
FIG. 6 is a cross-sectional view of another embodiment of a pressurized perfusion-enabled bioreactor as described herein.

FIGS. 4-5 show various aspects of an embodiment of a system 200 as described herein. As shown in FIG. 4, a transport housing is configured to seat a bioreactor 100 and a gas feed chamber 203 (which can also be a conical tissue culture tube in embodiments). The gas feed chamber 203 is pressurized with positive pressure to drive fluid (in particular gasses or a mixture of gasses at a given temperature and/or humidity range) from the connector 211 through a passage 205 (for example plastic tubing) and into the bioreactor 100 via the connector 111 (which can also comprise a one-way value). Fluid can be driven under pressure (positive pressure in particular) to the gas feed chamber 203 from a source (not pictured) through a valve 209 (which can be an adjustable valve) and supply line 207 into the gas feed chamber 203 via a connector 213.

FIG. 5 also shows a skirt 215 on the gas feed chamber for physical stabilization when placed vertically on a flat surface.

Example 4

FIGS. 6-9 depict another embodiment of a bioreactor 300 as described herein.

Figure 7:
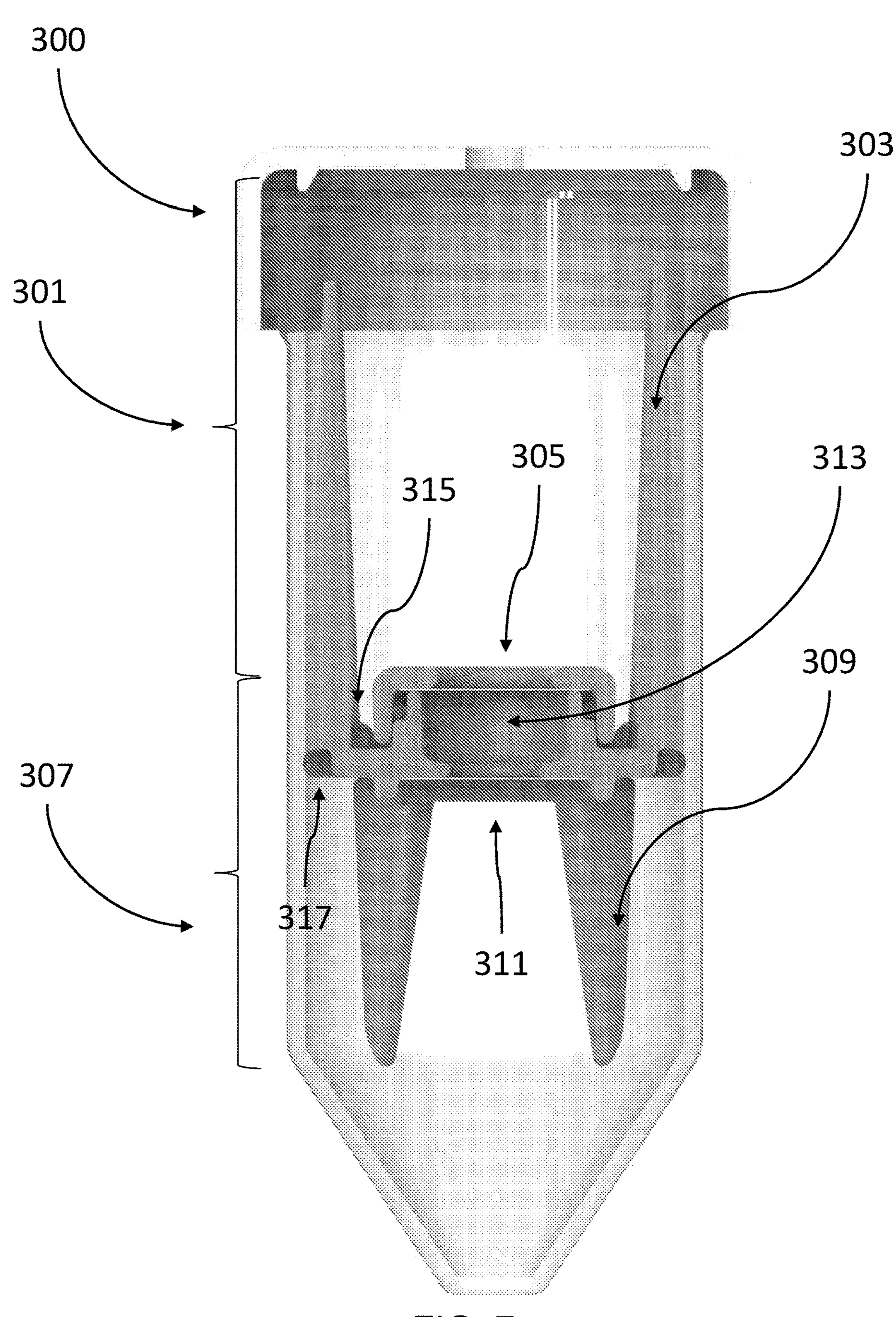
FIG. 7 is a side view of the embodiment of FIG. 6.
Figure 8:
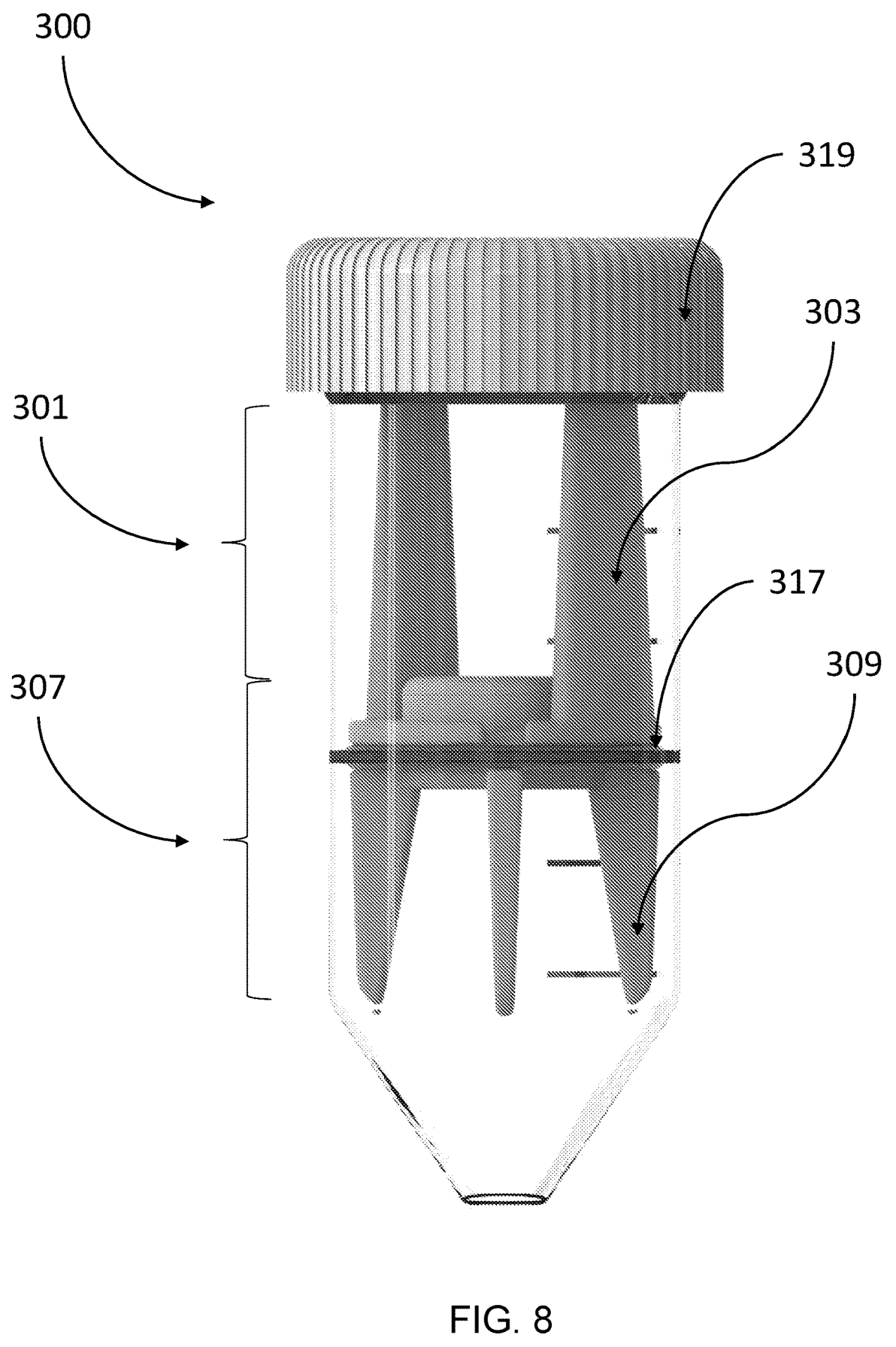
Figure 9:
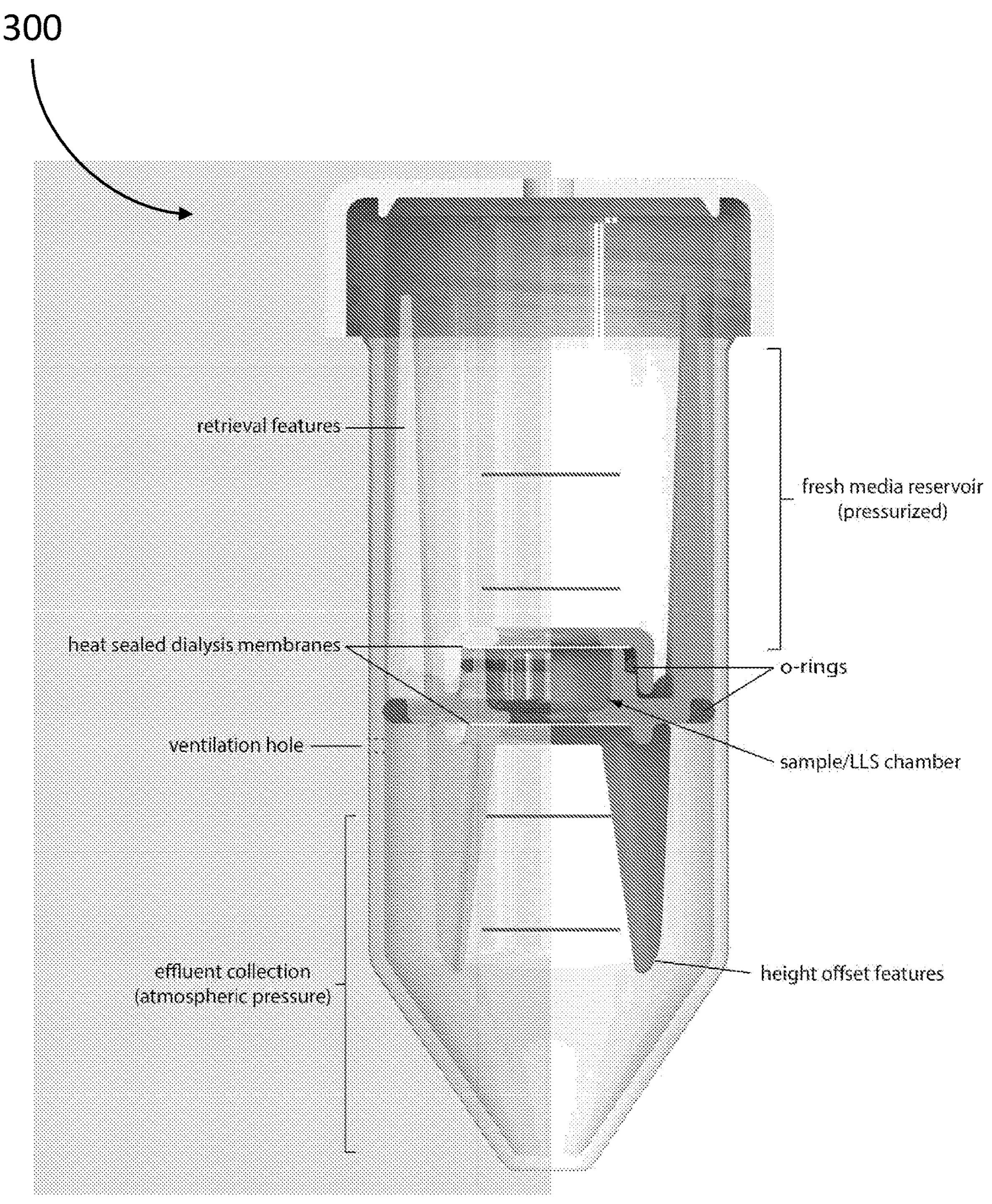
FIG. 9 is a split side/cross-sectional view of the embodiment of FIG. 6.

A cross-sectional view of an embodiment of a bioreactor 300 is shown in FIG. 7. As can be appreciated from the view of FIG. 7, an interlocked cap 301 and frame 307 are nested in the bioreactor 300. The cap 301 has a plurality of retrieval portions 303 and a central aperture 311. The frame 307 has a plurality of height offsets 309 and a central aperture 305. A sample chamber 313 is formed in between the cap 301 and frame 307 upon interlocking, with an inner seal 315 separating the cap 301 and frame 307, and an outer seal 317 separating the interlocked cap 301 and frame 307 from the outer walls of the bioreactor 300. A side view of the bioreactor 300 depicted in FIG. 7 is shown in FIG. 8 with the addition of a top 319 that seals the bioreactor 300. It is further noted that while aspects of the embodiment of the bioreactor 300 are depicted with annular and/or circular cross-sectional features (viewing down a longitudinal axis from top to bottom), such annular and/or circular geometry is not limiting.

Example 5

Figure 10:
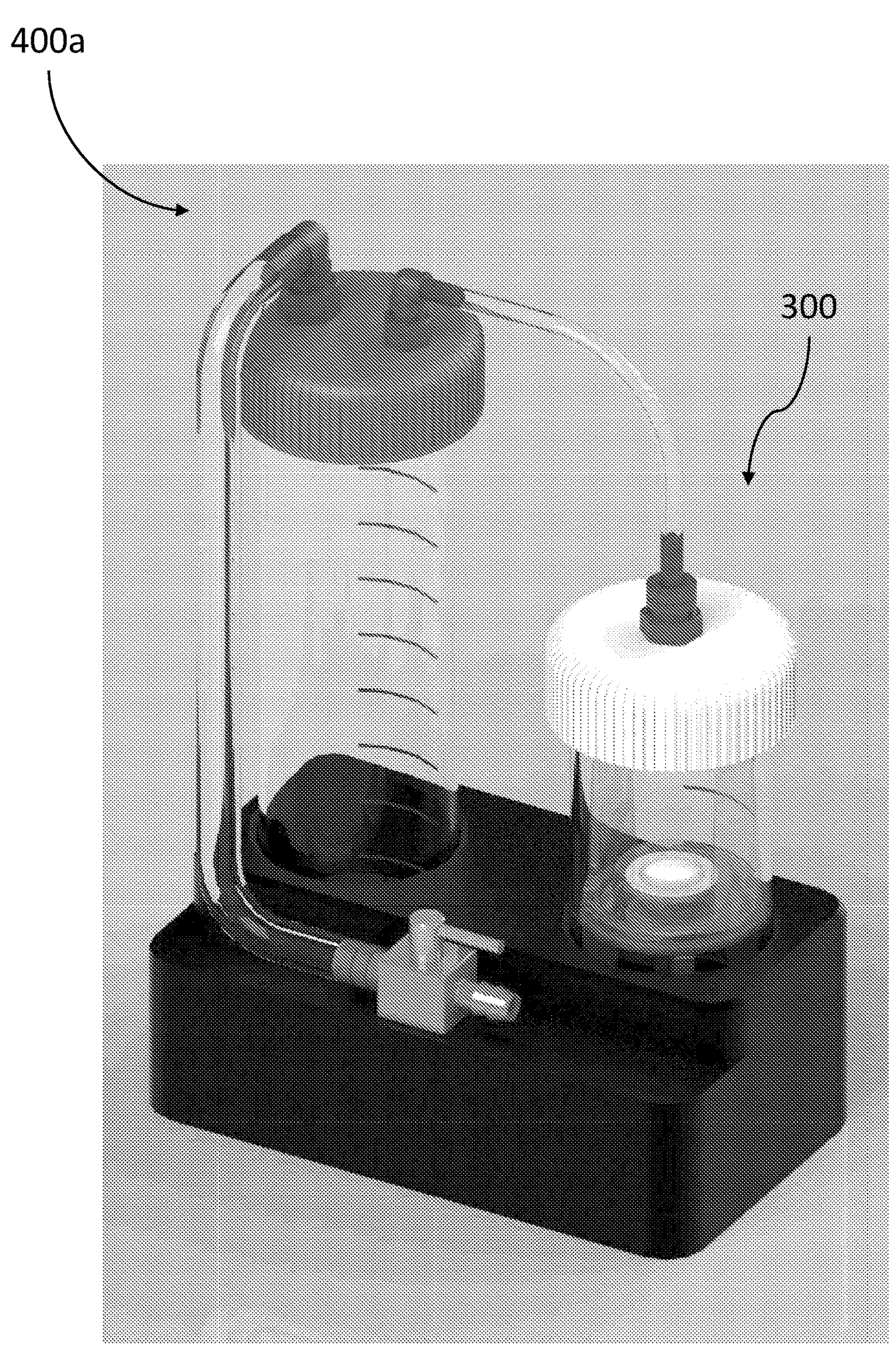
FIG. 10 is another embodiment of a system as described herein.
Figure 11:
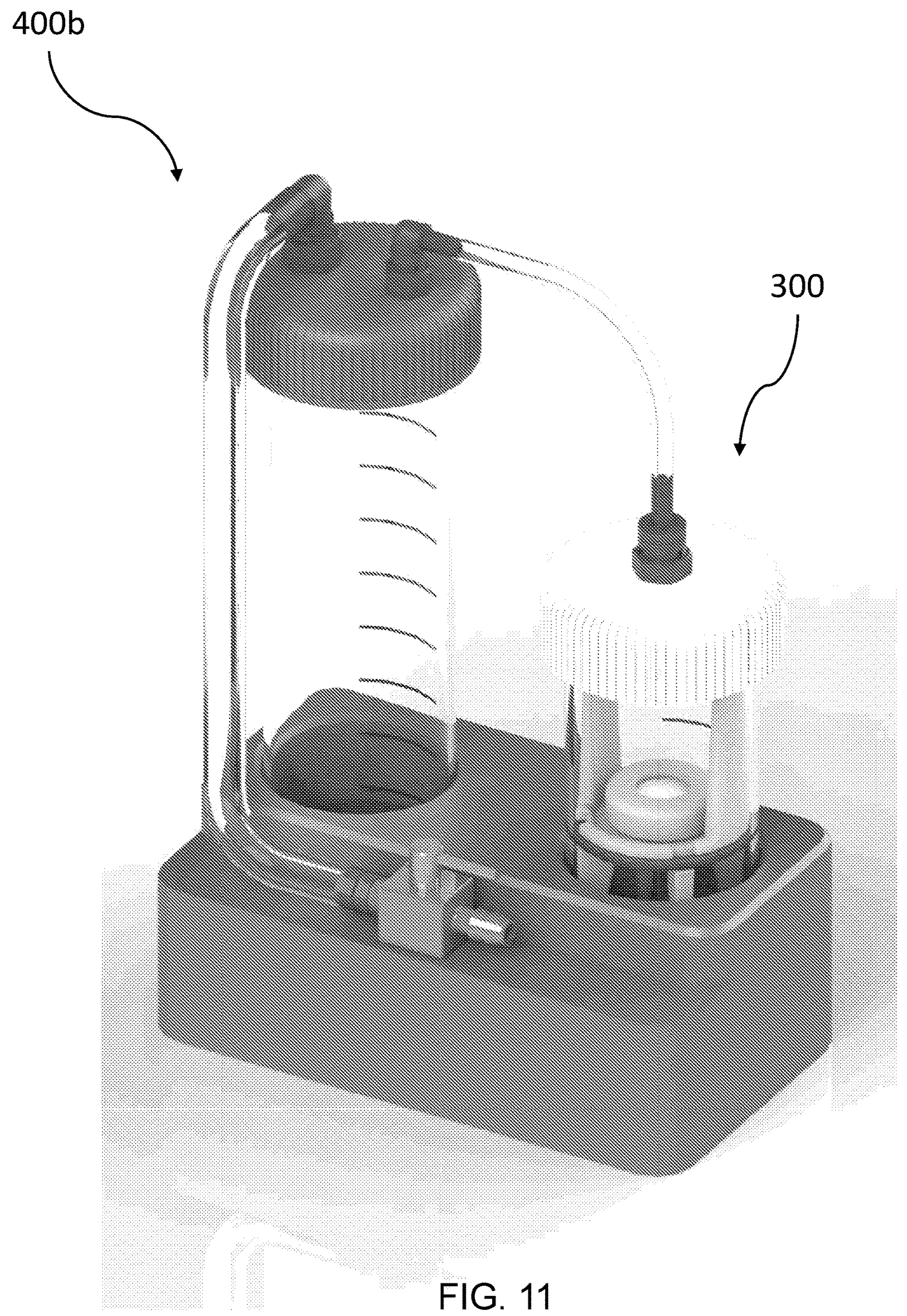
FIG. 11 is another embodiment of a system as described herein.

FIGS. 10-11 depict additional embodiments of systems 400*a* and 400*b* as described herein, substantially similar to the system 200 of FIGS. 4-5 (with identical features, colors/ anodization aside) but substituting bioreactor 100 (as shown in FIGS. 4-5) for bioreactor 300.

Example 6

Figure 12:
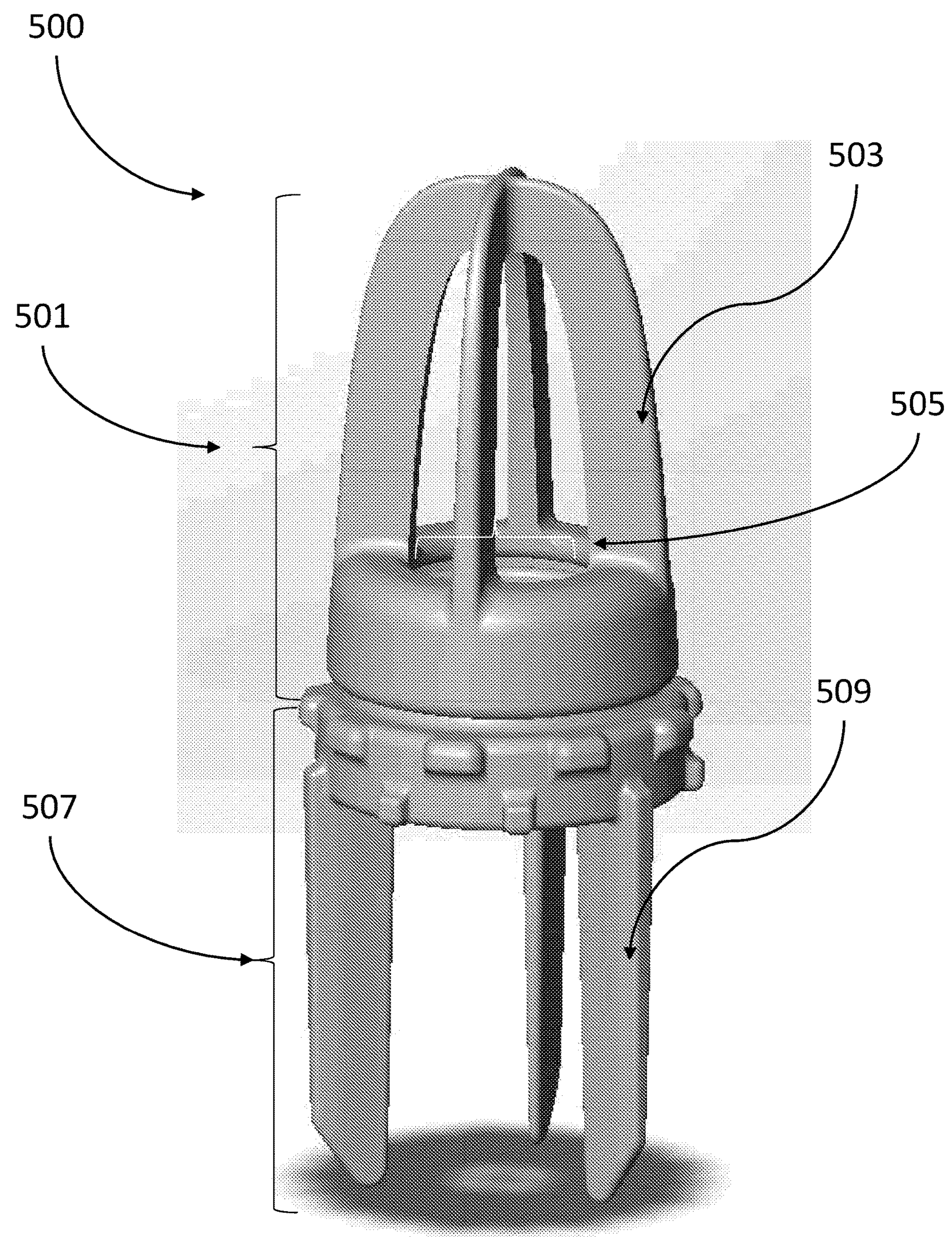
FIG. 12 is another embodiment of an interlocked cap and frame for bioreactors and systems as described herein.
Figure 13:
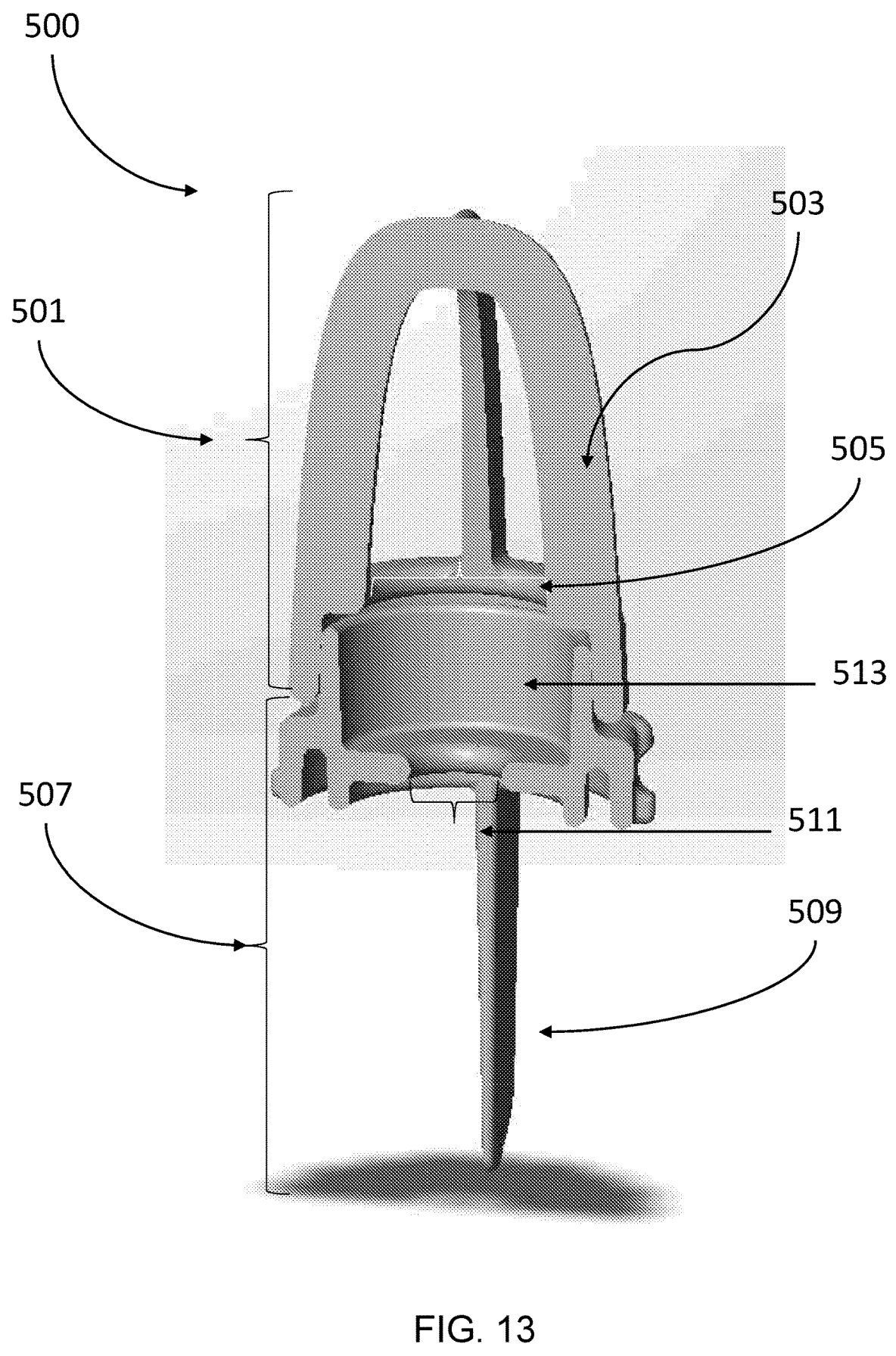
Figure 14:
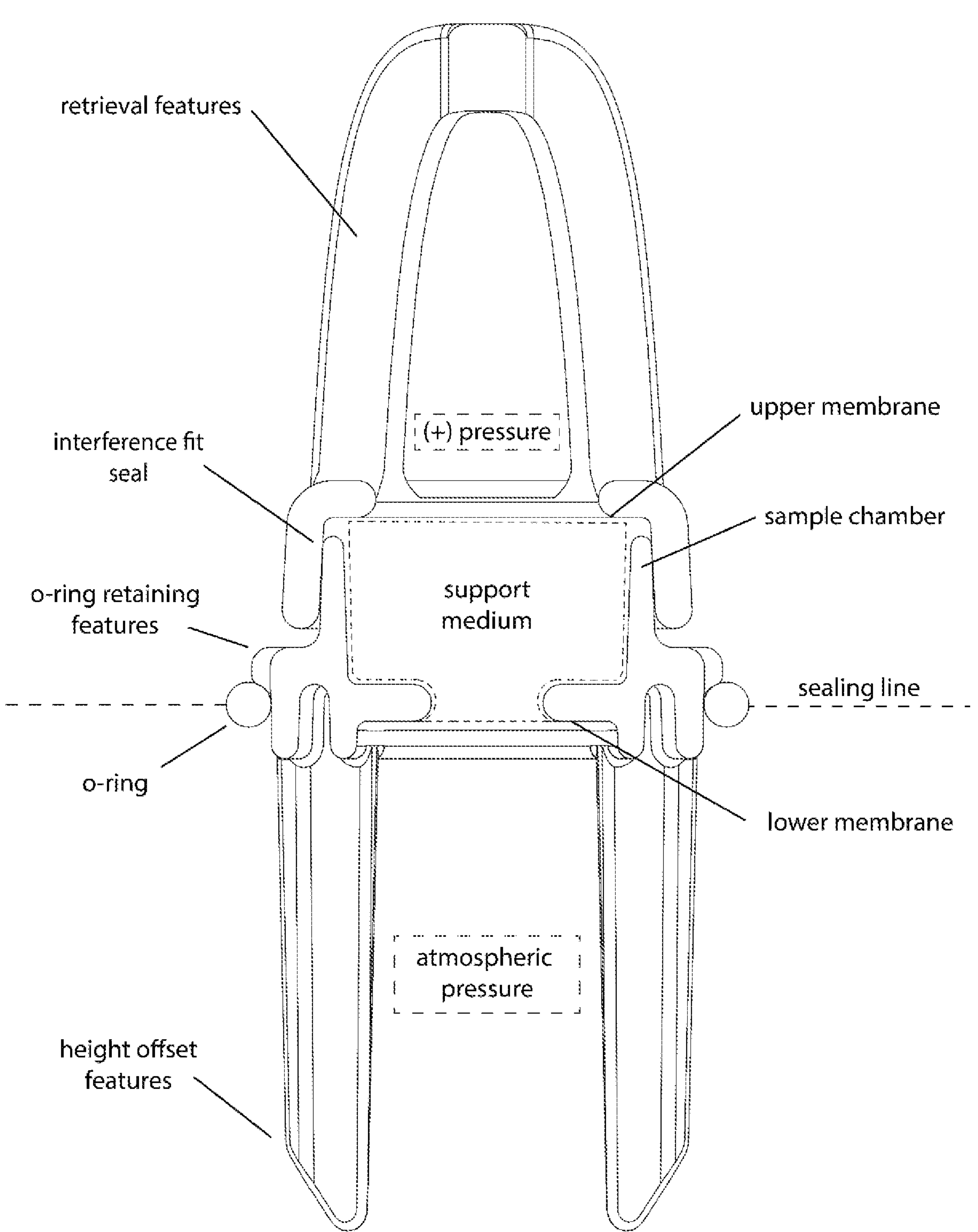
FIG. 14 is another view of the embodiment of FIG. 12.
Figures 15A, 15B, 15C, 15D, 15E:
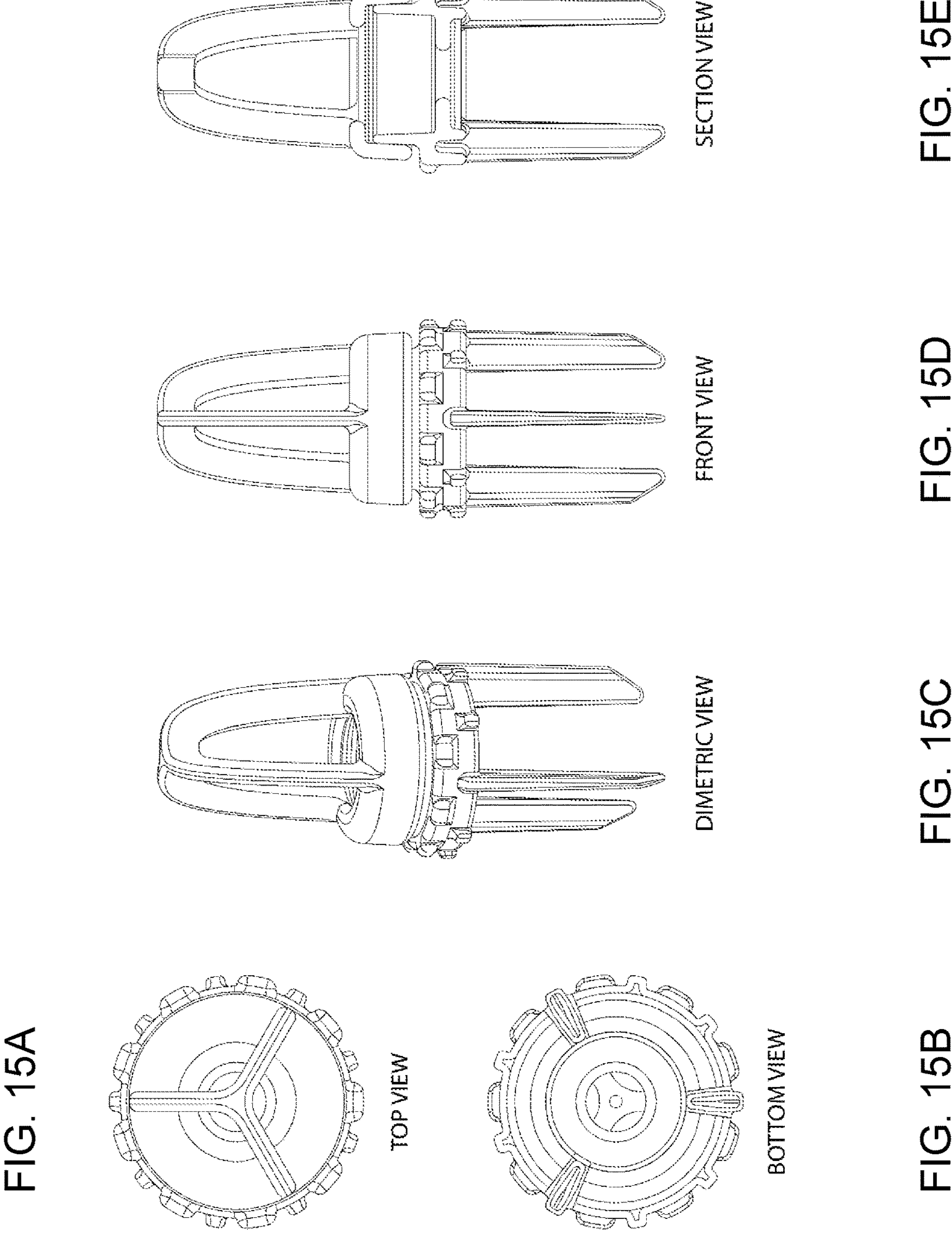
FIGS. 15A-15E show additional views of the embodiment of FIG. 12.

FIGS. 12-13 depict an embodiment of an interlocked cap/frame assembly 500 as described herein. As shown in FIG. 12, a cap 501 comprises a plurality of retrieval features 503 that converge and physically connect at a central apex to allow for simple retrieval from the bioreactor by a user. The central aperture 505 of the cap 501 is also depicted. The frame portion 507 is also shown with a plurality of height offsets 509.

The ribbed features depicted in FIG. 12 on the perimeter opposite the sample chamber are the outer seal (for example rubber O-ring) retaining features. In this embodiment, an O-ring can be used to seal the device with the interior of the centrifuge tube (inner wall of the bioreactor). The device must be slid into the tube from the top and then must stay in place when a pressure is applied. The ribs hold the O-ring in place so that when it is slid up or down in the tube it does not roll out of place.

FIG. 13 is a cross-sectional view that shows additional aspects of the interlocked cap and frame 500, in particular the central aperture 511 of the frame and the sample chamber 513 formed by interlocking the cap 501 and frame 507. It is further noted that while aspects of the embodiment of the bioreactor 500 are depicted with annular and/or circular cross-sectional features (viewing down a longitudinal axis from top to bottom), such annular and/or circular geometry is not limiting.

FIG. 14 and FIGS. 15A-15E are additional views of the embodiment of FIG. 12.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A positive pressure perfusion-enabled bioreactor, comprising:

a bioreactor having a central chamber bound by a high pressure side and a low pressure side and one or more walls; and an interlocking cap and frame in the central chamber, wherein the cap comprises a plurality of retrieval features arranged around a central cap aperture and extending toward an opening at the high pressure side of the bioreactor;

wherein the frame comprises a plurality of height offsets arranged around a central frame aperture and extending toward the low pressure side of the bioreactor in a direction opposite the retrieval features;

wherein the cap and frame are configured to interlock through an interference fit, forming an interlocked cap and frame, thereby aligning and forming a sample chamber in between the central frame aperture and the central cap aperture; and one or more membranes spanning the central frame aperture, the central cap aperture, or both.

2. The positive pressure perfusion-enabled bioreactor of claim 1, further comprising one or more inner seals separating one or more interlocked portions of the cap and the frame.

3. The positive pressure perfusion-enabled bioreactor of claim 1, further comprising one or more outer seals positioned in between the interlocked cap and frame and one or more outer walls of the bioreactor.

4. The positive pressure perfusion-enabled bioreactor of claim 1, further comprising a ventilation aperture in one or more outer walls of the bioreactor below one or more outer seals.

5. The positive pressure perfusion-enabled bioreactor of claim 1, further comprising a top configured to seal the opening of the bioreactor opposite the low pressure side.

6. The positive pressure perfusion-enabled bioreactor of claim 5, wherein the top is configured to receive fluid under positive pressure.

7. The positive pressure perfusion-enabled bioreactor of claim 6, wherein the fluid is a gas or mixture of gases.

8. The positive pressure perfusion-enabled bioreactor of claim 1, wherein the bioreactor is a conical tissue culture tube.

9. The positive pressure perfusion-enabled bioreactor of claim 1, wherein the bioreactor is a well of a tissue culture plate.

10. A positive pressure perfusion-enabled bioreactor system, comprising a bioreactor of claim 1; and a support medium in the sample chamber.

11. The positive pressure perfusion-enabled bioreactor system of claim 10, wherein the support medium comprises hydrogel particles dispersed in a liquid cell growth medium.

12. The positive pressure perfusion-enabled bioreactor system of claim 10, further comprising a fluid feed chamber configured to hold fluid that is provided to the bioreactor under positive pressure and a bioreactor feed line to provide fluid from the fluid feed chamber to the bioreactor through the top of the bioreactor.

13. The positive pressure perfusion-enabled bioreactor system of claim 12, further comprising a fluid feed line to provide fluid to the fluid feed chamber.

14. The positive pressure perfusion-enabled bioreactor system of claim 13, further comprising a valve operably connected with the fluid feed line to regulate fluid flow to the fluid feed chamber.

15. The positive pressure perfusion-enabled bioreactor system of claim 12, further comprising a system housing to hold and support the bioreactor and fluid feed chamber.

16. A method of using a positive pressure perfusion-enabled bioreactor, comprising:

providing a bioreactor;

seating a frame in an inner chamber of the bioreactor with height offsets extending towards the bioreactor bottom;

providing a support medium into a chamber of the frame and on top of a membrane spanning a central aperture of the frame;

placing a biological sample into support medium;

providing a cap and interlocking the cap with the frame.

17. The method of claim 16, further comprising sealing the chamber of the bioreactor with a top.

18. The method of claim 16, further comprising providing fluid under positive pressure to the chamber of the bioreactor.

* * * * *